(12) United States Patent
Fattinger

(10) Patent No.: US 11,946,930 B2
(45) Date of Patent: Apr. 2, 2024

(54) DEVICE FOR USE IN THE DETECTION OF BINDING AFFINITIES

(71) Applicant: Hoffmann-La Roche Inc., Little Falls, NJ (US)

(72) Inventor: Christof Fattinger, Blauen (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 884 days.

(21) Appl. No.: 15/733,485

(22) PCT Filed: Feb. 28, 2019

(86) PCT No.: PCT/EP2019/055008
§ 371 (c)(1),
(2) Date: Aug. 7, 2020

(87) PCT Pub. No.: WO2019/166562
PCT Pub. Date: Sep. 6, 2019

(65) Prior Publication Data
US 2021/0102940 A1 Apr. 8, 2021

(30) Foreign Application Priority Data
Mar. 1, 2018 (EP) .................................. 18159499

(51) Int. Cl.
*G01N 21/47* (2006.01)
*G01N 21/77* (2006.01)
*G01N 33/543* (2006.01)

(52) U.S. Cl.
CPC ... *G01N 33/54373* (2013.01); *G01N 21/4788* (2013.01); *G01N 21/7743* (2013.01)

(58) Field of Classification Search
CPC ......... G01N 33/54373; G01N 21/4788; G01N 21/7743
See application file for complete search history.

(56) References Cited

U.S. PATENT DOCUMENTS

| 4,876,208 A | 10/1989 | Gustafson et al. |
| 8,619,260 B2 | 12/2013 | Matejka et al. |
| 2016/0161477 A1* | 6/2016 | Fattinger .......... G01N 33/54373 422/69 |

FOREIGN PATENT DOCUMENTS

| EP | 0276968 A2 | 8/1988 |
| JP | S63277969 A | 11/1988 |

(Continued)

OTHER PUBLICATIONS

Gatterdam et al. (Sep. 25, 2017) "Focal Molography is a New Method for the In Situ Analysis of Molecular Interactions in Biological Samples", Nature Nanotechnology, 12:1089-1095 (8 pages).

(Continued)

*Primary Examiner* — Jill A Warden
*Assistant Examiner* — Michael Stanley Gzybowski
(74) *Attorney, Agent, or Firm* — Mintz, Levin, Cohn, Ferris, Glovsky and Popeo, P.C.

(57) ABSTRACT

A device for use in the detection of binding affinities comprises a substrate, a planar waveguide arranged thereon and having an outer surface. The device further comprises a grating for coupling coherent light of a predetermined wavelength into the planar waveguide such that the coherent light coupled into the planar waveguide propagates through the planar waveguide in a predetermined propagation direction. An evanescent field of the coherent light propagates along the outer surface of the planar waveguide. The outer surface of the planar waveguide has receptor molecules arranged thereon capable of binding target samples to the receptor molecules such that light of the evanescent field is diffracted by the target samples bound to the receptor molecules. The receptor molecules are arranged along a plurality of straight parallel lines such that a portion of the (Continued)

light of the evanescent field is diffracted by the target samples bound to the receptor molecules.

22 Claims, 8 Drawing Sheets

(56) References Cited

FOREIGN PATENT DOCUMENTS

| | | | |
|---|---|---|---|
| JP | H07169088 A | 7/1995 |
| JP | H08285851 A | 11/1996 |
| WO | WO-2001/071322 A3 | 9/2001 |
| WO | WO-2009/040746 A1 | 4/2009 |
| WO | WO-2010/022512 A1 | 3/2010 |
| WO | WO-2010/063116 A1 | 6/2010 |
| WO | WO-2013/107811 A1 | 7/2013 |
| WO | WO-2014/086789 A1 | 6/2014 |
| WO | WO-2014111521 A1 | 7/2014 |
| WO | WO-2015/004264 A1 | 1/2015 |
| WO | WO-2015/007674 A1 | 1/2015 |
| WO | 2015111458 A1 | 7/2015 |
| WO | WO-2015/096859 A1 | 7/2015 |
| WO | WO-2019/166562 A1 | 9/2019 |
| WO | 2020015872 A1 | 1/2020 |

OTHER PUBLICATIONS

Lai et al. (Aug. 1, 2008) "Label-Free Biosensor by Protein Grating Coupler on Planar Optical Waveguides", Optics Letters, 33(15):1735-1737.

Bruls, D. et al. (published online Oct. 2009). "Rapid integrated biosensor for multiplexed immunoassays based on actuated magnetic nanoparticles." Lab Chip 9:3504-3510.

Fattinger, C. (2014). "Focal molography: Coherent microscopic detection of biomolecular interaction." Physical Review X 4:031024-1-13.

Frutiger, A. et al. (Jan. 2019). "Principles for sensitive and robust biomoleculare interaction analysis: The limits of detection and resolution of diffraction-limited focal molography." Physical Review Applied 11:(2019) 014056-1-45.

Liscidini, M. et al. (Feb. 2009). "Analysis of Bloch-surface-wave assisted diffraction-based biosensors." Journal of the Optical Society American B, vol. 26(2):279-289.

Pawlak, M. et al. (2002). "Zeptosens' protein microarrays: A novel high performance microarray platform for low abundance protein analysis." Proteomics 2:383-393.

Written Opinion of the International Searching Authority dated Apr. 24, 2019 in International Application No. PCT/EP2019/055008, filed on Feb. 28, 2019.

Zhian, L. et al. (Aug. 1, 2008). "Label-free biosensor by protein grating coupler on planar optical waveguides." Optics Letters 33(15):1735-1737.

\* cited by examiner

DEVICE FOR USE IN THE DETECTION OF BINDING AFFINITIES

CROSS-REFERENCE TO RELATED APPLICATIONS

This application is a national stage application, filed under 35 U.S.C. § 371, of International Application No. PCT/EP2019/055008 filed on Feb. 28, 2019, which claims priority to European Patent Application No. EP 18159499.5, filed on Mar. 1, 2018, the content of which is hereby fully incorporated by reference.

FIELD

The present invention relates to a device and a system for use in the detection of binding affinities in accordance with the respective independent claim.

BACKGROUND

Such devices can be used, for example, as biosensors in a large variety of applications. One particular application is the detection or monitoring of binding affinities or processes. For example, with the aid of such biosensors various assays detecting the binding of target samples to binding sites can be performed. Typically, large numbers of such assays are performed on a biosensor at spots which are arranged in a two-dimensional microarray on the surface of the biosensor. The use of microarrays provides a tool for the simultaneous detection of the binding affinities or processes of different target samples in high-throughput screenings. For detecting the affinities of target samples to bind to specific binding sites, for example, the affinity of target molecules to bind to specific capture molecules, a large number of capture molecules is immobilised on the outer surface of the biosensor at individual spots, for example by ink-jet-like spotting or photolithography. Each spot forms an individual measurement zone for a predetermined type of target molecule. The binding of a target molecule to a specific type of capture molecule is detected and is used to provide information on the binding affinity of the target molecule with respect to the specific capture molecule.

A known technique for detecting binding affinities of target samples utilizes fluorescent labels. The fluorescent labels are capable of emitting fluorescent light upon excitation.

The emitted fluorescent light has a characteristic emission spectrum which is representative of the presence of the fluorescent label at a particular spot. The identified fluorescent label indicates that the labelled target molecule has bound to the particular type of capture molecule present at this spot.

A sensor for detecting labelled target samples is described in the article "Zeptosens' protein microarrays: A novel high performance microarray platform for low abundance protein analysis", Proteomics 2002, 2, S. 383-393, Wiley-VCH Verlag GmbH, 69451 Weinheim, Germany. The sensor described there comprises a planar waveguide arranged on a substrate. The planar waveguide has an outer surface with a plurality of capture molecules attached thereon. Moreover, the planar waveguide has a grating for coupling a beam of coherent light into the planar waveguide in a manner such that a beam of coherent light propagates along the planar waveguide. The coherent light propagates through the planar waveguide under total reflection with an evanescent field of the coherent light propagating along the outer surface of the planar waveguide. The depth of penetration of the evanescent field into the medium of lower refractive index at the outer surface of the planar waveguide is in the order of magnitude of a fraction of the wavelength of the coherent light propagating through the planar waveguide. The evanescent field excites the fluorescent labels of the labelled target samples bound to the capture molecules arranged on the surface of the planar waveguide. Due to the very small depth of penetration of the evanescent field into the optically thinner medium at the outer surface of the planar waveguide, only the labelled samples bound to the capture molecules immobilized on the outer surface of the planar waveguide are excited. The fluorescent light emitted from these labels is then detected with the aid of a CCD camera.

While it is principally possible to detect the binding affinities using fluorescent labels, this technique is disadvantageous in that the detected signal is produced by the fluorescent labels rather than by the binding partners themselves. In addition, labelling the target samples requires additional preparation steps. Moreover, labelled target samples are comparatively expensive. Another disadvantage is the falsification of the results caused by steric hindrance of the fluorescent labels at the target sample which might interfere with the binding of the target samples to the capture molecules. Further disadvantages are the falsification of the results due to photo-bleaching of the labels or quenching effects.

U.S. Pat. No. 8,619,260 discloses a label-free multi-grating resonant waveguide sensor for an optical reader system. Light from a light source is formed into an incident beam and directed to the resonant waveguide sensor to form a light spot thereon. The wavelength of the reflected light depends on the substances possibly located on the surface of the resonant waveguide sensor. The reflected light from the light spot on the resonant waveguide sensor is detected and analyzed for its wavelength with the use of a spectrometer which is usually rather expensive.

Many of the above-mentioned disadvantages have been overcome by the methods and devices disclosed in WO 2013/107811, WO 2014/086789, WO 2014/111521, WO 2015/004264 and WO 2015/007674. Instead of using labels and detect light emitted therefrom, diffracted coherent light from target samples bound to capture molecules is detected. As the amount of diffracted light is usually very small and more difficult to detect, especially in the presence of light other than the diffracted light, the capture molecules are typically arranged along a plurality of curved lines to cause the diffracted coherent light to constructively interfere in a focal point, where the diffracted light can be detected more reliably. However, the detection of the diffracted light still leaves room for further improvements, especially with respect to the positioning of the detector at the focal point. On one hand, the positioning of the detector must be very precise and requires a very high accuracy which may be in the range of one micrometer (μm) or even a fraction thereof. On the other hand, the detector is normally positioned at a very close distance from the waveguide. Typically, this distance is around 1 mm, thus resulting in constructional limitations.

SUMMARY

One object of the present invention is, therefore, to suggest a device and a system for use in the detection of binding affinities between a target sample and a receptor molecule which overcome or at least greatly reduce one or more of the disadvantages of the prior art described above.

In accordance with the invention, this object is achieved by a device and a system for use in the detection of binding affinities as it is specified by the features of the respective independent claim. Advantageous aspects of the device and system according to the invention are the subject of the dependent claims.

The device for use in the detection of binding affinities in accordance with the invention comprises a substrate and a leakproof planar waveguide arranged thereon and having an outer surface. A planar waveguide is a very thin waveguide (typically having a thickness in the range of 100 nanometers (nm) to a few micrometers (μm) only), and this is why the planar waveguide is arranged on a substrate—the substrate forms a support for the thin planar waveguide. A planar waveguide typically only allows a few modes or even only one specific mode to propagate through the planar waveguide.

The term 'leakproof' with respect to the planar waveguide means that once coherent light has been coupled into the planar waveguide the coherent light (the mode) propagating through the planar waveguide is securely guided in the planar waveguide by total internal reflection and does not leak out of the waveguide, so that practically the whole energy (except for the evanescent field) is guided in the planar waveguide and is prevented from leaking out of the waveguide (for example couple into adjacently arranged structures). Consequently, structures that allow energy to leak out of the waveguide during propagation of the light in the waveguide are not a 'planar waveguide' according to this invention. Planar waveguides typically have a high refractive index (e.g. a refractive index of more than 1.5, or even more than 1.8 or still higher), and this refractive index of the planar waveguide is obviously higher than the refractive index of the substrate on which it is arranged. The planar waveguide has a width and a length (typically it has a rectangular cross-sectional profile) and an outer surface opposite to the substrate on which it is arranged.

The device according to the invention further comprises a grating, and this grating is arranged on the planar waveguide (for example, the grating may be arranged on the outer surface of the planar waveguide opposite to the substrate and facing away from the substrate, or it may be arranged on the side of the planar waveguide facing the substrate). The grating comprises grating lines extending in the direction of the width of the planar waveguide (i.e. perpendicular to the length of the planar waveguide), and the grating period in the direction of the length of the planar waveguide (which corresponds to the predetermined propagation direction) is less than 1 micrometer (μm). The grating is for in operation coupling coherent light of a predetermined wavelength incident on the grating into the planar waveguide such that the coherent light coupled into the planar waveguide propagates through the planar waveguide in the predetermined propagation direction. This propagation direction, as mentioned, corresponds to the direction of the length of the planar waveguide. As also mentioned already, an evanescent field of the coherent light then propagates along the outer surface of the planar waveguide.

A decoupler is arranged on the outer surface of the planar waveguide spaced apart from the grating in the predetermined propagation direction by a distance of at least 10 micrometers (μm). In terms of wavelengths typically used (which may be in the UV-range up to the IR-range, for example in the range of some hundreds of nanometers, e.g. in the range of visible light) the decoupler is located quite a distance away from the grating. This is advantageous as is discussed in more detail further below.

The decoupler on the outer surface of the planar waveguide comprises receptor molecules arranged on (e.g. attached to) the outer surface of the planar waveguide. These receptor molecules are capable of binding target samples to the receptor molecules. The receptor molecules are arranged along a plurality of straight parallel lines which are spaced from each other such that in operation a portion of the coherent light of the evanescent field is diffracted by the target samples bound to the receptor molecules and is decoupled from the planar waveguide as a collimated beam of diffracted coherent light propagating away from the planar waveguide in a predetermined detection direction.

The decoupler on the outer surface of the planar waveguide further comprises filler molecules arranged on (e.g. attached to) the outer surface of the planar waveguide in interstices formed between the straight parallel lines along which the receptor molecules are arranged. The filler molecules are incapable of binding the target samples to the filler molecules.

The receptor molecules arranged along the predetermined lines and the filler molecules arranged in the interstices between the predetermined straight lines together form an optically smooth area on the surface of the planar waveguide. This optically smooth area has the same refractive index and a uniform height relative to the outer surface of the planar waveguide that varies by no more than 1 nanometer (nm). The term 'optically smooth area' means that this area does not form a grating or other structure that would lead to diffraction as long as no target samples are bound to the receptor molecules.

A grating may be formed by a substantial variation of the height in the area where the receptor molecules and the filler molecules are arranged (such variation must be in the range of the predetermined wavelength of the coherent light), or may be formed by regions of different refractive index in the said area. However, if there is no such variation of the height (or if there is a variation that is substantially smaller than the predetermined wavelength of the coherent light, and the specified variation of less than 1 nanometer is substantially smaller) and no variation of the refractive index, then the area does not cause diffraction and is called 'optically smooth'.

This property of 'optical smoothness' changes at the time the target molecules are bound to the receptor molecules while no target molecules are bound to the filler molecules (as these latter are incapable of binding the target molecules): At that time there is a variation in height which is in the range of the predetermined wavelength of the coherent light. The grating so formed represents an 'affinity modulated grating' since the grating is modulated by the binding affinity of the receptor molecules: The area of the decoupler where the receptor molecules and the filler molecules are arranged forms a grating at the time the target molecules are bound to the receptor molecules so that diffraction of a portion of the coherent light occurs and can be detected, while the same area of the decoupler does not form a grating (i.e. is 'optically smooth') as long as there are no binding events.

One of the advantages of the device according to the invention is that the diffracted portion of the coherent light forms a beam of collimated light propagating away from the planar waveguide so that this diffracted coherent light can be detected at a distance much farther away from the planar waveguide than is the case with prior art devices, so that detection of the diffracted light is much less dependent on the distance of a detector from the waveguide. A collimated beam is to be understood to comprise exactly parallel beams as well as beams which are diverging by no more than 3°, in particular by no more than 2°, more particularly by no more than 1°, and very particularly by no more than 0.5°. Detection thus becomes less sensitive as regards the positional arrangement of the detector (distance from the waveguide, exact position of the detector in the focal point). Consequently, a system for detecting binding affinities using the device according to the invention can be much easier from a constructional point of view when compared to prior art systems. This will be discussed in detail below when discussing the aspects of the system according to the invention.

The term 'predetermined detection direction' denotes the direction in which the collimated beam of diffracted coherent light is propagating away from the planar waveguide for detection. A detector can be (but does not have to be) placed in this direction. Accordingly, the predetermined detection direction is not necessarily the direction in which the detector must be arranged. For example, if a deflecting element such as a mirror is placed in the predetermined detection direction, the collimated beam is deflected in a different direction, in which the detector can be arranged.

For example, in case of a horizontally arranged planar waveguide the collimated beam of diffracted coherent light propagating away from the planar waveguide in the predetermined detection direction may propagate away from the planar waveguide downwardly or upwardly, or both. Although in the following by way of example a downwardly propagating collimated beam of coherent light will be discussed only, the discussion likewise applies for a collimated beam propagating upwardly away from the planar waveguide. Also, in case of an arrangement of the planar waveguide other than in a horizontal plane, the predetermined detection direction in which the diffracted light propagates away from the planar waveguide can be different, too.

Another advantage of the device according to the invention is that it allows for more additional options. For example, it allows to place additional equipment, for example magnetic equipment helping in accelerating the movement of target samples applied on the surface of the device towards the receptor molecules arranged on the surface of the planar waveguide (in this case, the target samples must comprise a magnetic label).

As mentioned, the grating for coupling the coherent light into the planar waveguide comprises (straight) grating lines extending in the direction of the width of the planar waveguide, so that the coherent light coupled into the planar waveguide propagates in a single predetermined propagation direction (i.e. in the direction of the length of the planar waveguide) within the planar waveguide towards the plurality of straight parallel lines along which the receptor molecules are arranged. Suitable physical structures representing such grating lines can be, for example, grooves, elongated protrusions or periodical changes of the refractive index of the planar waveguide.

As also mentioned already, the decoupler is arranged on the outer surface of the planar waveguide spaced apart from the grating in the predetermined propagation direction (i.e. in the direction of the length of the planar waveguide) by a distance of at least 10 micrometers (μm). In operation, it is advantageous to direct the coherent light emitted from a light source to the grating such that the straight parallel lines along which the receptor molecules are arranged are not directly exposed to light coming from the light source. Thus, the straight parallel lines along which the receptor molecules are arranged are only exposed to the light of the evanescent field propagating along the outer surface of the waveguide.

The grating for coupling the coherent light into the planar waveguide may not be located on the same outer surface of the planar waveguide on which the receptor molecules are arranged along the straight parallel lines, but may be located on the opposite outer surface of the planar waveguide where the planar waveguide abuts against the substrate.

The diffracted coherent light forming the collimated beam of coherent light propagating away from the waveguide has the same predetermined wavelength as has the coherent light coming from the light source immediately before being coupled into the planar waveguide, as long as the light coming from the light source and the diffracted light propagating away from the waveguide propagate in the same material, for example air, or vacuum, or in materials having the same refractive index.

The diffracted coherent light propagating away from the planar waveguide constructively interferes in the predetermined detection direction in any plane normal to the predetermined detection direction. Viewed from each of the receptor molecules there is constructive interference always in the same direction. In other words, the term 'constructively interferes in any plane normal to the predetermined detection direction' means that the coherent light of the collimated beam in any plane normal to the predetermined detection direction has the same phase.

A further advantage of the device according to the invention is that light reflected by the planar waveguide or reflected by the substrate does not disturb the detection of the diffracted coherent light propagating away from the planar waveguide, because the device can be configured such that the predetermined detection direction is different from the direction of light reflected either by the planar waveguide or by the substrate. Therefore, beam stops preventing reflected light from interfering with light diffracted by the target samples bound to the receptor molecules are not needed.

As is discussed in detail further below, the distance between the straight parallel lines can be configured so as to result in a particular predetermined detection direction of the collimated beam of diffracted coherent light.

In general, the detection of binding affinities according to the invention is neither limited to specific types of target samples nor to any type of receptor molecules, but rather the binding characteristics of e.g. molecules, proteins, DNA etc. as target samples can be analyzed with respect to any suitable type of receptor molecule on the planar waveguide.

The arrangement of the receptor molecules along the straight parallel lines represents the optimal case in which all receptor molecules are exactly arranged on the ideal straight parallel lines. The optimal arrangement of the receptor molecules is associated with a maximum intensity or amount of the diffracted coherent light propagating away from the planar waveguide in the predetermined detection direction. In practice, the arrangement of the receptor molecules may deviate to some extent from such optimal arrangement while the collimated beam of diffracted coherent light is still sufficiently pronounced.

The substrate has mainly the function of supporting the planar waveguide which can be extremely thin.

Such substrate can be transparent or non-transparent (opaque). In the latter case, the device can be used upside-down with the non-transparent substrate being arranged above the planar waveguide, so that neither the coherent light coupled into the planar waveguide nor the collimated beam of diffracted coherent light must pass through the substrate.

The coherent light can be visible light or ultraviolet (UV) or infrared (IR) light.

As already mentioned, a collimated beam of diffracted coherent light does not only denote an exactly parallel beam of diffracted coherent light but may also comprise a slightly diverging beam of diffracted coherent light which is diverging by no more than 3° (degrees), in particular by no more than 2°, more particularly by no more than 1°, and very particularly by no more than 0.5°. In this case, the predetermined propagation direction may comprise a bundle of slightly diverging propagation directions diverging by no more than 3°, or 2°, or 1°, or 0.5°, respectively. When being extrapolated against the direction of actual propagation of the collimated beam of diffracted coherent light, such slightly diverging beam converges into a virtual focal point and, accordingly, the slightly diverging beam of diffracted coherent light appears to come from a light source arranged at this virtual focal point.

For instance, the virtual focal distance of the virtual focal point, measured from the planar waveguide, is larger than ten times the diameter of the collimated beam of diffracted coherent light at the planar waveguide, in particular larger than fifteen times the diameter of the collimated beam of diffracted coherent light at the planar waveguide, more particularly larger than thirty times the diameter of the collimated beam of diffracted coherent light at the planar waveguide, and very particularly larger than sixty times the diameter of the collimated beam of diffracted coherent light at the planar waveguide. The virtual focal point can have infinite distance from the planar waveguide (this being equivalent to a parallel collimated beam).

Accordingly, the term 'straight parallel lines' does not only comprise lines which are exactly straight but also comprises lines minimally deviating from being exactly straight in case these lines cause the afore-mentioned slightly diverging collimated beam.

Such lines are geometrically defined by the equation $$(x_j - x_0) = \pm \frac{\sqrt{n_C^2(N^2 - n_C^2)(y_j^2 + f^2) + (n_C\lambda)^2(j_0 + j)^2} - \lambda N(j_0 + j)}{N^2 - n_C^2}$$

wherein
  $\lambda$ is the vacuum wavelength of the coherent light,
  N is the effective refractive index of the coherent light propagating through the planar waveguide; N depends on the thickness and the refractive index of the planar waveguide, the refractive index of the substrate, the refractive index of a medium on the outer surface of the planar waveguide and the polarization of the guided mode,
  f is the virtual focal length,
  $x_0$ is an offset of the predetermined lines in x-direction,
  $n_c$ is the refractive index of a medium on the outer surface of the planar waveguide,
  $j_0$ is a fixed integer, and
  j is a running integer that indicates the index of the respective predetermined line.

The ± sign in the equation means that in case of plus sign there is a virtual focal point and in case of a minus sign there is a real focal point, with the latter case representing a converging beam of diffracted coherent light in the direction of propagation of the diffracted light, which does not form part of the instant invention.

For the plus sign, the receptor molecules are arranged along these lines in a manner such that the difference in optical path length from the light source to the virtual focal point is an integer multiple of the wavelength of the propagating coherent light.

In a preferred embodiment of the invention, the virtual focal length f is not only larger than the diameter of the area which comprises the straight parallel lines, but the focal length f may even approach infinity (this representing the case where the lines are exactly straight). In general, the condition $f \gg 2\,(x_j^2 + y_j^2)^{1/2}$ for the virtual focal length should be fulfilled (the focal length f is larger more than an order of magnitude, preferably more than twenty times the diameter of the area that comprises the straight parallel lines).

A further advantage of the device according to the invention is that in case of a slightly diverging collimated beam of diffracted coherent light such collimated beam has a growing diameter as the distance from the planar waveguide increases, and thereby the usefulness of optical elements like lenses which can be arranged in the path of such slightly diverging beam of diffracted coherent light increases with an increasing distance of such optical elements from the device.

According to an aspect of the device according to the invention, the filler molecules may be identical with the receptor molecules except that they are deactivated so as to be incapable of binding the target molecules to the filler molecules. 'Deactivation' in this regard refers to any method suitable to change the binding capability of the receptor molecules before or after their attachment (immobilization) on the outer surface of the planar waveguide. Deactivation can be achieved, for example, by exposing those receptor molecules arranged in the interstices between the predetermined straight lines to UV light in order to achieve that they are no longer capable of binding the target samples (for example with the aid of a mask). Deactivation of the receptor molecules arranged in the interstices between the predetermined straight lines can be achieved, for example, by an alteration of the binding region of the receptor molecules. In essence, therefore, the deactivated receptor molecules arranged in the interstices between the predetermined straight lines are identical with those receptor molecules arranged along the predetermined straight lines— except that they are deactivated. This is an effective way of forming the optically smooth area of the decoupler (before the target samples are bound to the receptor molecules arranged along the predetermined straight lines).

It has been mentioned already, that in accordance with one aspect the grating for coupling the coherent light into the planar waveguide may be arranged on the outer surface of the planar waveguide opposite to the substrate, i.e. on the same surface of the planar waveguide on which the receptor molecules are arranged (but spaced therefrom).

According to another aspect of the device according to the invention, there may be a minimum distance $d_{min}$ between adjacently arranged straight parallel lines of the plurality of straight parallel lines, measured in the predetermined propagation direction, which may be defined according to the equation $$d_{min} = \lambda/(N - n_c \sin \alpha)$$

wherein
  $\alpha$ is a longitudinal angle between the predetermined detection direction and a normal to the outer surface of the planar waveguide, measured in the predetermined propagation direction,
  $\lambda$ is the vacuum wavelength of the coherent light, N is the effective refractive index of the coherent light propagating through the planar waveguide, and $n_c$ is the refractive index of a medium on the outer surface of the planar waveguide and wherein the adjacently arranged straight parallel lines of the plurality of straight parallel lines are arranged at a distance d from each other which is an integer multiple of the minimum distance $d_{min}$.

For each predetermined detection direction of the collimated beam of diffracted coherent light propagating away from the planar waveguide there exists a corresponding minimum distance $d_{min}$ between adjacent straight parallel lines. The straight parallel lines may be arranged equidistantly spaced from one another by that minimum distance $d_{min}$. In this case, a maximum amount of diffracted coherent light per area of the device can be achieved. This may lead to a high signal-to-noise ratio at the detector and consequently to a high sensitivity regarding the determination of the binding affinities, as will be shown later in more detail in the context of the discussion of the respective features and aspects of the system according to the invention. However, in order to simplify manufacture of the device the distance d between adjacent ones of the straight parallel lines can be an integer multiple of the minimum distance $d_{min}$. It is well within the scope of the invention to have non-uniform distances d between adjacent straight parallel lines, as long as the respective distances d between adjacent straight parallel lines is an integer multiple of the minimum distance $d_{min}$.

According to a further aspect of the device according to the invention, the distance d between the adjacently arranged straight parallel lines of the plurality of straight parallel lines, measured in the predetermined propagation direction, may be in the range of $\lambda/2<d<2\lambda/3$, or is an integer multiple thereof.

For example, the wavelength of the coherent light may be in the range of 300 nm (nanometers) to 3000 nm, more specifically in the visible range of the light, i.e. between 400 nm and 700 nm, or in the near infrared range of the spectrum, i.e. between 700 nm and 2000 nm. For example, the wavelength λ in the planar waveguide may be at typical wavelengths of laser diodes emitting visible or near infrared light, e.g. about 635 nm, or about 850 nm, or about 976 nm, or about 1064 nm, or about 1625 nm. In the case of λ=635 nm, the distance d may, for example, be about 350 nm, and in the case of λ=1625 nm the distance d may, for example, be about 900 nm, wherein the term "about" is to be understood as including typical tolerances of present manufacturing technologies of such structures. The advantage of such small distances between adjacent ones of the straight parallel lines is that the overall size of the device according to the invention can be kept very small. Also, the areas where the straight parallel lines are arranged on the outer surface of the planar waveguide (decoupler) can be kept very small, for example they can be smaller than 1 mm² (square millimeter) and may each comprise several hundred up to some thousands of straight parallel lines with receptor molecules arranged along these lines, while still leaving space for the grating to be arranged on the same outer surface of the planar waveguide.

According to yet a further aspect of the device according to the invention, the longitudinal angle α may be in the range of 1°<α<20°.

More preferably, the longitudinal angle α may be between 2° and 10°. The advantage thereof is that in case of a similar angle of the coherent light emitted from a light source and impinging onto the optical coupler, there will be virtually no reflections of coherent light in the predetermined detection direction.

According to still a further aspect of the device according to the invention, the angle β between the straight parallel lines and the predetermined propagation direction of the coherent light in the plane of the planar waveguide may be in the range of 60°<β<120°, measured in the plane of the planar waveguide (or to be even more precise in the plane of the outer surface of the planar waveguide). More preferably, the angle β may be between 75° and 105°.

The advantage thereof is that in case of a similar angle β between the straight parallel lines and the predetermined propagation direction of the coherent light in the plane of the planar waveguide, the diffracted coherent light forming the collimated beam of coherent light propagating away from the waveguide will propagate in directions away from the waveguide that are separated from the propagation direction of the coherent light emitted from the light source and impinging onto the grating and that may be partially reflected at the outer surface of the planar waveguide opposite to the outer surface on which the receptor molecules are arranged.

The straight parallel lines may be arranged parallel to the wave fronts of the coherent light propagating through the planar waveguide, or to say it in other words, the straight parallel lines can be arranged normal to the predetermined propagation direction of the coherent light in the plane of the planar waveguide. Alternatively, the straight parallel lines may include an angle β other than 90° with respect to the predetermined propagation direction of the coherent light in the plane of the planar waveguide. Advantageously, the angle β can be configured for any desired detection direction of the collimated beam of diffracted coherent light.

According to a further aspect of the device according to the invention, the device may comprise a plurality of spatially separated decouplers arranged on the outer surface of the planar waveguide opposite to the substrate. Each spatially separated decoupler may have a said plurality of straight parallel lines, with the receptor molecules being arranged along the respective plurality of straight parallel lines and with the filler molecules being arranged in the interstices between the respective plurality of straight parallel lines.

In operation and with the target samples bound to the receptor molecules, a collimated beam of diffracted coherent light propagates away from each spatially separated decoupler on the outer surface of the planar waveguide. Advantageously, with a device having a plurality of spatially separated decouplers with receptor molecules arranged along a plurality of straight parallel lines, a plurality of collimated beams of diffracted coherent light propagate away from the device and provide the opportunity for being detected simultaneously, i.e. a single device with a plurality of spatially separated decouplers can be used to detect multiple binding affinities simultaneously.

Each spatially separated decoupler has an individual plurality of straight parallel lines, defined by the distance d between adjacent lines and the angle β, which can be identical to or different from each of the other pluralities of straight parallel lines of the other spatially separated decouplers. In operation, the spatially separated decouplers are arranged on the outer surface of the planar waveguide such that all of them are exposed to the evanescent field of the coherent light propagating through the planar waveguide.

As already mentioned, the device according to the invention can be very small while still allowing for a plurality of spatially separated decouplers to be arranged on the outer surface of the planar waveguide. For example, on a surface of the size of 1 cm$^2$ (square centimeter), several tens or hundreds or thousands or even ten thousands of such spatially separated areas may be arranged while still leaving space for one or more grating to be arranged on the same outer surface of the planar waveguide. In total up to several millions of said spatially separated decouplers can be arranged on a single device according to the invention.

The size and shape of the spatially separated decouplers arranged on the same device does not have to be the same for all spatially separated decouplers. The shape of the decouplers can be for example circular, elliptical, polygonal, rectangular or quadratic.

According to a yet further aspect of the device according to the invention, the adjacent straight parallel lines of the plurality of straight parallel lines of at least one spatially separated decoupler of the plurality of spatially separated decouplers may be arranged at a first distance $d_1$ from each other which is an integer multiple of a first minimum distance $d_{min1}$, and the adjacent straight parallel lines of the plurality of straight parallel lines of at least one other spatially separated decoupler of the plurality of spatially separated decouplers may be arranged at a second distance $d_2$ from each other which is an integer multiple of a second minimum distance $d_{min2}$, wherein the first minimum distance $d_{min1}$ and the second minimum distance $d_{min2}$ may be different from each other.

A device according to the invention with at least two spatially separated decouplers having the straight parallel lines arranged at different minimum distances $d_{min1}$ and $d_{min2}$ has the advantage that the collimated beams of diffracted coherent light propagating away from the respective spatially separated area have different detection directions, especially different longitudinal angles $\alpha_1$ and $\alpha_2$. As will be discussed in more detail below, depending on the requirements of the system employed to detect the collimated beams of diffracted coherent light, the detection directions of the collimated beams of diffracted light can be configured such that the collimated beams of diffracted light impinge on the detector of the system either at larger or smaller distances than the distances of the spatially separated decouplers. Or to say it in other words, it is possible to decouple the spacing of different decouplers on the device and the spacing of different collimated beams of diffracted coherent light impinging on a detector of a system for detecting the diffracted coherent light.

According to a further aspect of the device according to the invention, the straight parallel lines of at least one spatially separated decoupler of the plurality of spatially separated decouplers may include a first angle $\beta_1$ with the predetermined propagation direction of the coherent light in the planar waveguide, and wherein the straight parallel lines of at least one other spatially separated decoupler of the plurality of spatially separated decouplers may include a second angle $\beta_2$ with the predetermined propagation direction of the coherent light in the planar waveguide, wherein the first angle $\beta_1$ may be different from the second angle $\beta_2$.

A device with at least two spatially separated decouplers having the straight parallel lines arranged at different angles $\beta_1$ and $\beta_2$ has the advantage that the collimated beams of diffracted coherent light propagating away from the respective spatially separated decouplers have different detection directions, especially different transversal angles $\gamma_1$ and $\gamma_2$. As will be discussed in more detail below, depending on the requirements of the system employed to detect the collimated beams of diffracted coherent light, the detection directions of the collimated beams of diffracted light can be configured such that the collimated beams of diffracted light impinge on the detector of the system either at larger or smaller distances than the distances of the spatially separated decouplers on the device according to the invention. Or to say it in other words, it is possible to decouple the spacing of different decouplers on the device and the spatial spacing of different collimated beams of diffracted coherent light when impinging on a detector of a system for detecting the diffracted coherent light.

It goes without saying that more than two spatially separated decouplers can be arranged on the same planar waveguide, and the straight parallel lines of these decouplers may be arranged at a different angle $\beta_1$, i.e. in each of these decouplers the straight parallel lines are arranged at a different angle $\beta_1$. Alternatively, the straight parallel lines of some of the decouplers may be arranged at the same angle $\beta$, but for each of these decouplers the minimum distance $d_{min}$ between adjacently arranged straight parallel lines is different, so that the angle $\alpha$ of the diffracted beam is different for each of them. So with the aid of the angle $\beta$ and the minimum distance $d_{min}$ two parameters are available with the aid of which it is possible to spatially separate the diffracted beams of coherent light diffracted by the decouplers, while at the same time all of these decouplers may be arranged on the outer surface of the same planar waveguide. Even more, these decouplers may even be arranged in the same section of the planar waveguide, as will become more evident from the discussion of these sections further below.

According to a further aspect of the device according to the invention, at least one spatially separated decoupler of the plurality of spatially separated decouplers may have a first type of receptor molecules capable of binding a first type of the target samples, and wherein at least one other spatially separated decoupler of the plurality of spatially separated decouplers may have a second type of receptor molecules capable of binding the first type of the target samples or the second type of the target samples, wherein the first type of the receptor molecules may be different from the second type of the receptor molecules.

In many applications, it is desirable to know if a substance contains different types of target samples. Advantageously, the testing of the substance for the presence of different target samples can be done with a single device according to the invention. Therefore, one single device may comprise a plurality of spatially separated decouplers, with different spatially separated decouplers comprising different types of receptor molecules such that for each different type of target samples at least one spatially separated decoupler exists comprising a type of receptor molecules capable of binding to said type of target samples. It is also possible to use different types of receptor molecules in different decouplers, wherein the different types of receptor molecules are capable of binding to identical types of target samples, e.g. for the purpose of checking the binding affinities of different types of receptor molecules to an identical type of target samples.

According to a further aspect of the device according to the invention, the device may comprise a plurality of spatially separated sections on the outer surface of the planar waveguide, each spatially separated section comprising one or more of said spatially separated decouplers and a said grating.

Having a plurality of sections each comprising a grating and one or more of such spatially separated decouplers provides for the opportunity to consecutively read out such sections one after the other with a suitable system. Therefore, further advantages of such a plurality of spatially spaced sections as well as the reading out of the sections become apparent when discussing the corresponding system aspects further below.

The size of a section may typically be between 1 mm$^2$ and 100 mm$^2$ (square millimeters). However, the size of the section can be smaller or larger without departing from the scope of this invention. In total, up to 10000 spatially separated sections can be arranged on one device according to the invention. Advantageously, each section comprises more than 10 spatially separated decouplers. For best utilization of the space on a device, the shape of a section can be polygonal, rectangular or quadratic.

The intensity of the coherent light propagating in the predetermined propagation direction through the planar waveguide decreases during propagation. Therefore, the evanescent field also decreases in the predetermined propagation direction. For example, after a distance of 8 mm from the grating the intensity of the evanescent field may have decreased to one third of the intensity at the grating. Therefore, depending on the size of the spatially separated decouplers arranged in one section, preferably no more than 10 areas are placed one after another in a row in the predetermined propagation direction before a different section having its own grating starts.

According to a further aspect of the device according to the invention, the device may comprise a hydrogel layer arranged on the outer surface of the planar waveguide opposite to the substrate and may cover the receptor molecules. The hydrogel layer may be configured to allow the target samples to diffuse therethrough for allowing them to bind to the receptor molecules. The hydrogel layer may further be configured to prevent molecules exceeding a predetermined size which is larger than the size of the target samples from diffusing therethrough.

According to a further aspect of the device according to the invention, in an area where the grating is arranged a cover layer may be arranged on the outer surface of the planar waveguide opposite to the substrate, the cover layer being transparent to light of the predetermined wavelength. An absorption layer may be arranged on the transparent cover layer, the absorption layer being absorptive to light of the predetermined wavelength.

Any coherent light that is not coupled into the planar waveguide may possibly lead to stray light that may reach the array detector and would therefore falsify the measurement of the light diffracted at the target samples bound to the receptor molecules. To avoid such stray light, the absorption layer extincts such coherent light that has passed through the transparent layer to avoid that stray light possibly resulting from such non-coupled portions of impinging light may reach the array detector.

According to a further aspect of the device according to the invention, that outer surface of the planar waveguide opposite to the outer surface on which the binding sites are arranged may be covered with an anti-reflection coating. Such anti-reflection coating, for example a $\lambda/4$-layer, further reduces reflections that may occur and that may also possibly lead to unwanted light at the array detector.

The invention further relates to a system for the detection of binding affinities. The system comprises a device according to the invention. Further, the system comprises a light source for emitting coherent light of a predetermined wavelength. The light source and the device are arranged relative to one another such that the coherent light emitted from the light source is coupled into the planar waveguide via the grating of the device. In addition, the system comprises a lens for focusing the collimated beam of diffracted coherent light propagating away from the planar waveguide in a predetermined detection direction into a focal point. Also, the system comprises a detector positioned optically downstream of the lens in the focal point of the lens, for detecting the diffracted coherent light of the collimated beam focused into the focal point of the lens. Finally, the system comprises an evaluation device for providing a signal representative of the diffracted coherent light detected by the detector. The signal is indicative of the affinity of the target samples to bind to the receptor molecules.

In operation, coherent light that has been diffracted by target samples bound to the receptor molecules arranged along the straight parallel lines on the outer surface of the planar waveguide can be detected in the focal point of the lens as a measure for the affinity of the target samples to bind to the receptor molecules. For example, the intensity or the amount of the diffracted coherent light provided at the focal point of the lens is detected and compared to a known intensity of coherent light which has been diffracted by the receptor molecules only, i.e. without target samples bound thereto, or by a physical grating on the outer surface of the planar waveguide.

The change in intensity or the amount of diffracted coherent light is representative of (i.e. is a measure for) the affinity of target samples to bind to the receptor molecules since the intensity or the amount of light at the focal point of the lens is significantly different when target samples have bound to the receptor molecules. This allows for the detection of target samples.

The light source can be a laser or a laser diode. In case of parallel coherent light being emitted from the light source, the diameter of said parallel beam may be 500 μm, for example.

The lens can be an optical lens. The aperture of the lens captures the amount of light focused in the focal point.

The detector may be an array detector. For example, the detector can be a CCD image sensor a CMOS image sensor or a time of flight image sensor, i.e. an array detector that incorporates time-of-flight discrimination of the detected light. The detector is positioned at the focal point of the lens and is arranged to extend perpendicular to the optical axis of the lens.

Providing a signal representative of the diffracted coherent light detected by the detector includes also displaying a signal which is representative of the diffracted coherent light detected by the detector.

No spectrometer is needed as no shift or change in the frequency spectrum of the coherent light occurs within the system according to the invention. Also, no pinholes are necessary for blocking unwanted light.

In operation, there can be multiple collimated beams of diffracted coherent light at the same time, and the system is then suitable to detect multiple collimated beams of diffracted coherent light at the same time.

Due to the simplicity of the system according to the invention, the system is especially suitable for a cost effective operation at the 'point of care', i.e. at the point where the testing of a substance for the presence of target samples is most desirable and possible without the need to transport the substance possibly containing the target samples to a central laboratory.

According to one aspect of the system according to the invention, the system may further comprise a scanner and de-scanner being arranged in an optical path between the light source and the planar waveguide (proximate to the planar waveguide) for directing the coherent light emitted from the light source towards the grating in a direction such that the amount of the coherent light coupled into the planar waveguide is maximal.

The scanner and de-scanner is a device which is capable of both directing coherent light emitted from the light source towards the grating and directing the collimated beam of diffracted coherent light propagating away from the planar waveguide, by deflecting both the coherent light emitted from the light source and the collimated beam of diffracted coherent light propagating away from the planar waveguide in the same manner.

The advantage of such scanner and de-scanner is that in case the device according to the invention is not positioned in the system exactly as intended but at a certain unwanted inclination, the scanner and de-scanner is capable of correcting for such an unwanted inclination and therefore ensures that there will be no detection error caused by any unwanted inclination of the device.

The scanner and de-scanner is arranged proximate to the planar waveguide at a working-distance from the planar waveguide in the range of some mm (millimeters) up to about 1 cm or even 10 cm (centimeters). The maximum possible working distance depends on the diameter of the collimated beam of diffracted coherent light propagating away from the planar waveguide in the predetermined detection direction and the aperture of the lens. For example, for a spatially separated area with a diameter of 20 μm (micrometers) and comprising about 60 straight parallel lines, the working-distance may be 1 mm. For a spatially separated area with a diameter of 1 mm and comprising about 3000 straight parallel lines, the working distance may be 5 cm. In any case, the working distance of the system according to the invention is much larger than any working distance of a prior art system using planar waveguides and diffracted light to determine binding affinities.

According to a further aspect of the system according to the invention, the system may comprise a mirror. The mirror has a front surface configured to reflect the collimated beam of diffracted coherent light towards the lens. The rear surface of the mirror may be configured to allow the coherent light emitted from the light source to pass through the mirror. The mirror may be arranged in an optical path of the diffracted coherent light between the scanner and de-scanner and the lens and in an optical path of the coherent light emitted from the light source between the light source and the scanner and de-scanner.

The mirror may increase the detection accuracy as less scattered light may impinge on the detector. Further, the mirror may allow for a more compact constructional design of the detection system.

According to a further aspect of the system according to the invention, the scanner and de-scanner may comprise a pivotable mirror and a telescopic lens arrangement. The telescopic lens arrangement may have two further lenses arranged in an optical path of the diffracted coherent light between the planar waveguide and the pivotable mirror. The system may further comprise an additional mirror arranged in an optical path of the coherent light emitted from the light source between the light source and the pivotable mirror. The additional mirror may be configured to reflect the coherent light emitted from the light source, and may further be configured to allow the collimated beam of diffracted coherent light to pass through the additional mirror.

The pivotable mirror or the pivotable mirror together with the telescopic lens arrangement can be embodied in form of a MEMS (microelectromechanical system). A typical size of such a mirror can be 2 mm×2 mm. For example, the mirror can be pivoted by 1°-2° through voltage-control.

According to yet a further aspect of the system according to the invention, the system may further comprise an actuator for consecutively positioning the optical coupler of each spatially separated section of the plurality of spatially separated sections of the device in the path of the coherent light emitted from the light source such that the coherent light emitted from the light source may be consecutively coupled into the planar waveguide at the respective spatially separated section.

The actuator for consecutively positioning the optical coupler of each spatially separated section provides the opportunity to consecutively 'read out' the respective sections. To 'read out' means to detect the diffracted coherent light propagating away from the spatially separated decouplers of a particular section in form of multiple collimated beams at the respective focal points.

The actuator can be controlled to read out a specific number of sections or all sections in a predetermined manner or sequence.

According to a further aspect of the system according to the invention, the system may further comprise at least one magnet which is movably arranged for being positioned in proximity to the receptor molecules or remote from the receptor molecules. In one embodiment of the system according to the invention, the magnet is placed at a first position corresponding to the position of the decoupler but on a side of the planar waveguide opposite to the side where the receptor molecules are arranged on the surface of the planar waveguide, or at a second position also corresponding to the position of the decoupler but on the same side of the planar waveguide where the receptor molecules are arranged on the surface of the planar waveguide, or at a third position in which the magnet is arranged remote from the path of the coherent light from the light source to the grating as well as remote from the path of the collimated beam of diffracted coherent light from the planar waveguide to the detector, and remote from the path of the coherent light from the grating to the decoupler.

This embodiment is advantageous in that magnetically labelled target samples can be moved to the receptor molecules more rapidly. With the magnet being arranged in the first position, the magnetically labelled target samples are moved to the receptor molecules with the aid of the magnetic field where they possibly bind to the receptor molecules. Subsequently, target samples not bound to the receptor molecules are removed by arranging the magnet in the second position. Thereafter, the magnet is removed out of the path of any light in order to allow for the detection of the binding affinity. Transportation of magnetically labelled samples is described, for example, in the article "Rapid integrated biosensor for multiplexed immunoassays based on actuated magnetic nanoparticles" by D. M. Bruls et. al., published in the journal "The Royal Society of Chemistry", 2009, 9, page 3504-3510.

In accordance with another aspect, the invention relates to a device and a system for use in the detection of binding affinities as is described in the following.

The device for use in the detection of binding affinities comprises a substrate and a planar waveguide arranged thereon and having an outer surface. The device further comprises an optical coupler for coupling coherent light of a predetermined wavelength into the planar waveguide such that the coherent light coupled into the planar waveguide propagates through the planar waveguide in a predetermined propagation direction. An evanescent field of the coherent light propagates along the outer surface of the planar waveguide. The outer surface of the planar waveguide has binding sites located thereon capable of binding target samples to the binding sites such that light of the evanescent field is diffracted by target samples bound to the binding sites. The binding sites are arranged along a plurality of straight parallel lines which are spaced from each other such that a portion of the light of the evanescent field is diffracted by target samples bound to the binding sites and forms a collimated beam of diffracted coherent light propagating away from the planar waveguide in a predetermined detection direction.

One of the advantages of such device is that a portion of the diffracted coherent light forms a beam of collimated light propagating away from the planar waveguide so that this portion of the diffracted coherent light can be detected at a distance much farther away from the planar waveguide than is the case with prior art devices, so that detection of the diffracted light is much less dependent on the distance of a detector from the waveguide. A collimated beam is to be understood to comprise parallel beams as well as beams which are diverging by no more than 3°, in particular by no more than 2°, more particularly by no more than 1°, and very particularly by no more than 0.5°. Detection thus becomes less sensitive as regards the positional arrangement of the detector (distance from the waveguide, exact position of the detector in the focal point). Consequently, a system for detecting binding affinities using the device according to the invention can be much easier from a constructional point of view when compared to prior art systems. This will be discussed in detail below when discussing the aspects of the system according to the invention.

The predetermined detection direction denotes the direction in which the collimated beam of diffracted coherent light is propagating away from the planar waveguide for detection. A detector can be (but does not have to be) placed in this direction. Accordingly, the predetermined detection direction is not necessarily the direction in which the detector must be arranged. For example, if a deflecting element such as a mirror is placed in the predetermined detection direction, the collimated beam is deflected in a different direction, in which the detector can be arranged.

For example, in case of a horizontally arranged planar waveguide the collimated beam of diffracted coherent light propagating away from the planar waveguide in the predetermined detection direction may propagate away from the planar waveguide downwardly or upwardly, or both. Although in the following by way of example a downwardly propagating collimated beam of coherent light will be discussed only, the discussion likewise applies for a collimated beam propagating upwardly away from the planar waveguide. Also, in case of an arrangement of the planar waveguide other than in a horizontal plane, the predetermined detection direction in which the diffracted light propagates away from the planar waveguide can be different, too.

Another advantage of such device is that it allows for more additional options. For example, it allows to place additional equipment, for example magnetic equipment helping in accelerating the movement of target samples applied on the surface of the device towards the binding sites arranged on the very surface of the planar waveguide (in this case, the target samples must comprise a magnetic label).

The optical coupler may comprise any physical or biological structure (e.g. grating) allowing for coupling the coherent light of a predetermined wavelength into the planar waveguide. The coherent light impinging on the planar waveguide may be divergent or collimated. Depending thereon, a suitable form of physical or biological structure, for example straight or curved (grating) lines, can be configured such that the coherent light coupled into the planar waveguide propagates in a single predetermined propagation direction within the planar waveguide towards the plurality of straight parallel lines along which the binding sites are arranged. Physical structures can be, for example, grooves, elongated protrusions or periodical changes of the refractive index of the planar waveguide. Biological structures can be, for example, target samples bound to binding sites arranged along lines on the planar waveguide (however, these target samples bound to binding sites of the coupler are not to be mixed-up with the target samples that are intended to be bound to the binding sites arranged along the straight parallel lines for detection of the binding affinity).

Preferably, the optical coupler is not arranged in a zone of the device where the straight parallel lines are arranged. In operation, it is advantageous to direct the coherent light emitted from a light source in a manner to the optical coupler such that the straight parallel lines (along which the target samples bound to the binding sites are arranged) are not directly exposed to light coming from the light source but rather in a manner such that the straight parallel lines are only exposed to the light of the evanescent field propagating along the outer surface of the waveguide.

Preferably, the optical coupler may not be located on the same outer surface of the planar waveguide on which the binding sites are arranged along the straight parallel lines, but may be located on the opposite outer surface of the planar waveguide where the planar waveguide abuts against the substrate.

The diffracted coherent light forming the collimated beam of coherent light propagating away from the waveguide has the same predetermined wavelength as has the coherent light coming from the light source immediately before being coupled into the planar waveguide, as long as the light coming from the light source and the diffracted light propagating away from the waveguide propagates in the same material, for example air, or vacuum, or in materials having the same refractive index.

The diffracted coherent light propagating away from the planar waveguide constructively interferes in the predetermined detection direction in any plane normal to the predetermined detection direction. Viewed from each binding site, there is constructive interference always in the same direction from each biding site. In other words, "constructively interferes in any plane normal to the predetermined detection direction" means that the coherent light of the collimated beam in any plane normal to the predetermined detection direction has the same phase.

A further advantage of such device is that light reflected by the planar waveguide or reflected by the substrate does not disturb the detection of the diffracted coherent light propagating away from the planar waveguide, because the device can be configured such that the predetermined detection direction is different from the direction of light reflected either by the planar waveguide or by the substrate. Therefore, beam stops preventing reflected light from interfering with light diffracted by the target samples bound to the binding sites are not needed.

As will be discussed in detail later, the distance between the straight parallel lines can be configured so as to result in a particular predetermined detection direction of the collimated beam of diffracted coherent light.

In general, "binding sites" are locations on the outer surface of the planar waveguide to which a target sample may bind (or binds in case of binding affinity). The detection of binding affinities is neither limited to specific types of target samples nor to any type of binding sites, but rather the binding characteristics of e.g. molecules, proteins, DNA etc. as target samples can be analyzed with respect to any suitable type of binding site on the planar waveguide.

The arrangement of the binding sites along the straight parallel lines represents the optimal case in which all binding sites are exactly arranged on the ideal straight parallel lines. The optimal arrangement of the binding sites is associated with a maximum intensity or amount of the diffracted coherent light propagating away from the planar waveguide in the predetermined detection direction. In practice, the arrangement of the binding sites may deviate to some extent from such optimal arrangement while the collimated beam of diffracted coherent light is still sufficiently pronounced.

The substrate has mainly the function of supporting the planar waveguide which can be extremely thin.

Such substrate can be transparent or non-transparent (opaque). In the latter case, the device can be used upside-down with the non-transparent substrate being arranged above the planar waveguide, so that neither the coherent light coupled into the planar waveguide nor the collimated beam of diffracted coherent light must pass through the substrate.

The coherent light can be visible light or ultraviolet (UV) or infrared (IR) light.

As already mentioned, a collimated beam of diffracted coherent light may comprise a slightly diverging beam of diffracted coherent light which is diverging by no more than 3°, in particular by no more than 2°, more particularly by no more than 1°, and very particularly by no more than 0.5°. In this case, the predetermined propagation direction may comprise a bundle of slightly diverging propagation directions diverging by no more than 3°, or 2°, or 1°, or 0.5°, respectively. When being extrapolated against the direction of actual propagation of the collimated beam of diffracted coherent light, such slightly diverging beam converges into a virtual focal point and, accordingly, the slightly diverging beam of diffracted coherent light appears to come from a light source arranged at this virtual focal point.

In some embodiments, the virtual focal distance of the virtual focal point, measured from the planar waveguide, is larger than ten times the diameter of the collimated beam of diffracted coherent light at the planar waveguide, in particular larger than fifteen times the diameter of the collimated beam of diffracted coherent light at the planar waveguide, more particularly larger than thirty times the diameter of the collimated beam of diffracted coherent light at the planar waveguide, and very particularly larger than sixty times the diameter of the collimated beam of diffracted coherent light at the planar waveguide. The virtual focal point can have infinite distance from the planar waveguide (this being equivalent to a parallel collimated beam).

Accordingly, the term "straight parallel lines" does not only comprise lines which are exactly straight but also comprises lines minimally deviating from being exactly straight in case these lines cause the afore-mentioned slightly diverging collimated beam.

Such lines are geometrically defined by the equation $$(x_j - x_0) = \pm \frac{\sqrt{n_C^2(N^2 - n_C^2)(y_j^2 + f^2) + (n_C\lambda)^2(j_0 + j)^2} - \lambda N(j_0 + j)}{N^2 - n_C^2}$$

wherein
λ is the vacuum wavelength of the propagating light,
N is the effective refractive index of the guided mode in the planar waveguide; N depends on the thickness and the refractive index of the planar waveguide, the refractive index of the substrate, the refractive index of a medium on the outer surface of the planar waveguide and the polarization of the guided mode,
f is a virtual focal length,
$x_0$ is an offset of the predetermined lines in x-direction,
$n_c$ is the refractive index of the medium on the outer surface of the planar waveguide,
$j_0$ is a fixed integer, and
j is a running integer that indicates the index of the respective predetermined line.

The ± sign in the equation means that in case of plus sign lines there is a virtual focal point and in case of a minus sign there is a real focal point, with the latter case representing a converging beam of diffracted coherent light in the direction of propagation of the diffracted light, which does not form part of the instant invention.

For the plus sign, the binding sites are arranged along these lines in a manner such that the difference in optical path length from the light source to the virtual focal point is an integer multiple of the wavelength of the propagating light.

In a preferred embodiment, the virtual focal length f is not only larger than the diameter of the area which comprises the straight parallel lines, but the focal length f may even approach infinity (this representing the case where the lines are exactly straight). In general, the condition $f \gg (x_j^2 + y_j^2)^{1/2}$ for the virtual focal length should be fulfilled (the focal length f is larger more than an order of magnitude, preferably more than twenty times the diameter of the area that comprises the straight parallel lines).

A further advantage of such device is that in case of a slightly diverging collimated beam of diffracted coherent light such collimated beam has a growing diameter as the distance from the planar waveguide increases, and thereby the utilization of optical elements like lenses, which can be arranged in the path of such slightly diverging beam of diffracted coherent light, increases with an increasing distance of such optical elements from the device.

According to one aspect of such device, there is a minimum distance $d_{min}$ between adjacently arranged straight parallel lines of the plurality of straight parallel lines, measured in the predetermined propagation direction, which is defined according to the equation $$d_{min} = \lambda/(N - n_c \sin \alpha)$$

wherein
α is a longitudinal angle between the predetermined detection direction and a normal to the outer surface of the planar waveguide, measured in the predetermined propagation direction,
λ is the vacuum wavelength of the propagating light,
N is the effective refractive index of the guided mode in the planar waveguide, and
$n_c$ is the refractive index of the medium on the outer surface of the planar waveguide and wherein adjacent straight parallel lines of the plurality of straight parallel straight lines are arranged at a distance d from each other which is an integer multiple of the minimum distance $d_{min}$.

For each predetermined detection direction of the collimated beam of diffracted coherent light propagating away from the planar waveguide there exists a corresponding minimum distance $d_{min}$ between adjacent straight parallel lines. The straight parallel lines may be arranged equidistantly spaced from one another by that minimum distance $d_{min}$. In this case, a maximum amount of diffracted coherent light per area of the device can be achieved. This may lead to a high signal-to-noise ratio at the detector and consequently to a high sensitivity regarding the determination of the binding affinities, as will be shown later in more detail in the context of the discussion of the respective features and aspects of the system. However, in order to simplify manufacture of the device the distance d between adjacent ones of the straight parallel lines can be an integer multiple of the minimum distance $d_{min}$. It is well within the scope of the invention to have non-uniform distances d between adjacent straight parallel lines, as long as the respective distances d between adjacent straight parallel lines is an integer multiple of the minimum distance $d_{min}$.

According to a further aspect of such device, the distance d between the adjacent ones of the straight parallel lines of the plurality of straight parallel lines, measured in the predetermined propagation direction, is in the range of $\lambda/2 < d < 2\lambda/3$, or is an integer multiple thereof.

For example, the wavelength of the coherent light may be in the range of 300 nm (nanometers) to 3000 nm, more specifically in the visible range of the light, i.e. between 400 nm and 700 nm, or in the near infrared range of the spectrum, i.e. between 700 nm and 2000 nm. For example, the wavelength $\lambda$ in the planar waveguide may be at typical wavelengths of laser diodes emitting visible or near infrared light, e.g. about 635 nm, or about 850 nm, or about 976 nm, or about 1064 nm, or about 1625 nm. In the case of $\lambda=635$ nm, the distance d may, for example, be about 350 nm, and in the case of $\lambda=1625$ nm the distance d may, for example, be about 900 nm, wherein the term "about" is to be understood as including typical tolerances of present manufacturing technologies of such structures. The advantage of such small distances between adjacent ones of the straight parallel lines is that the overall size of the device according to the invention can be kept very small. Also, the areas where the straight parallel lines are arranged on the device can be kept very small, for example they can be smaller than 1 mm² (square millimeter) and may each comprise several hundred up to some thousands of straight parallel lines with binding sites arranged thereon, while still leaving space for an optical coupler to be arranged on the same device or in the same area.

According to yet a further aspect of such device, the longitudinal angle $\alpha$ is in the range of $1° < \alpha < 20°$.

More preferably, the longitudinal angle $\alpha$ may be between 2° and 10°. The advantage thereof is that in case of a similar angle of the coherent light emitted from a light source and impinging onto the optical coupler, there will be virtually no reflections of coherent light in the predetermined detection direction.

According to still a further aspect of such device, the angle $\beta$ between the straight parallel lines and the predetermined propagation direction of the coherent light in the plane of the planar waveguide is in the range of $60° < \beta < 120°$. More preferably, the angle $\beta$ may be between 75° and 105°.

The advantage thereof is that in case of a similar angle $\beta$ between the straight parallel lines and the predetermined propagation direction of the coherent light in the plane of the planar waveguide, the diffracted coherent light forming the collimated beam of coherent light propagating away from the waveguide will propagate in directions away from the waveguide that are separated from the propagation direction of the coherent light emitted from the light source and impinging onto the optical coupler and that may be partially reflected at the outer surface of the planar waveguide opposite to the outer surface on which the binding sites are located.

The straight parallel lines may be arranged parallel to the wave fronts of the coherent light propagating through the planar waveguide, or to say it in other words, the straight parallel lines can be arranged normal to the predetermined propagation direction of the coherent light in the plane of the planar waveguide. Alternatively, the straight parallel lines may include an angle $\beta$ other than 90° with respect to the predetermined propagation direction of the coherent light in the plane of the planar waveguide. Advantageously, the angle $\beta$ can be configured for any desired detection direction of the collimated beam of diffracted coherent light.

According to a further aspect of such device, the device comprises a plurality of spatially separated areas arranged on the outer surface of the planar waveguide. Each spatially separated area has a said plurality of straight parallel lines with binding sites arranged along the respective plurality of straight parallel lines.

In operation and with target samples bound to binding sites, a collimated beam of diffracted coherent light propagates away from each spatially separated area on the surface of the planar waveguide. Advantageously, with a device having a plurality of spatially separated areas with binding sites arranged along a plurality of straight parallel lines, a plurality of collimated beams of diffracted coherent light propagate away from the device and provide the opportunity for being detected simultaneously, i.e. a single device with a plurality of spatially separated areas can be used to detect multiple binding affinities simultaneously.

Each spatially separated area has an individual plurality of straight parallel lines, defined by the distance d between adjacent lines and the angle $\beta$, which can be identical to or different from each of the other pluralities of straight parallel lines of the other spatially separated areas. In operation, the spatially separated areas are arranged on the planar waveguide such that they are exposed to the evanescent field of the coherent light propagating through the planar waveguide.

As already mentioned, such device can be very small while still allowing for a plurality of spatially separated areas to be arranged on the planar waveguide. For example, on a surface of the size of 1 cm², several tens or hundreds or thousands or even ten thousands of such spatially separated areas may be arranged while still leaving space for one or more optical couplers to be arranged on the same device. In total up to several millions of said spatially separated areas can be arranged on a single device according to the invention.

The size or shape of the spatially separated areas arranged on the same device does not have to be the same for all spatially separated areas. The shape of the areas can be for example circular, elliptical, polygonal, rectangular or quadratic.

According to a yet further aspect of such device, the adjacent straight parallel lines of the plurality of straight parallel lines of at least one spatially separated area of the plurality of spatially separated areas are arranged at a first distance $d_1$ from each other which is an integer multiple of a first minimum distance $d_{min1}$, and the adjacent straight parallel lines of the plurality of straight parallel lines of at least one other spatially separated area of the plurality of spatially separated areas are arranged at a second distance $d_2$ from each other which is an integer multiple of a second minimum distance $d_{min2}$, wherein the first minimum distance $d_{min1}$ and the second minimum distance $d_{min2}$ are different from each other.

A device with at least two spatially separated areas having the straight parallel lines arranged at different minimum distances $d_{min1}$ and $d_{min2}$ has the advantage that the collimated beams of diffracted coherent light propagating away from the respective spatially separated area have different detection directions, especially different longitudinal angles $\alpha_1$ and $\alpha_2$. As will be discussed in more detail below, depending on the requirements of the system employed to detect the collimated beams of diffracted coherent light, the detection directions of the collimated beams of diffracted light can be configured such that the collimated beams of diffracted light impinge on the detector of the system either at larger or smaller distances than the distances of the spatially separated areas. Or to say it in other words, it is possible to decouple the spacing of different areas of straight parallel lines on the device and the spacing of different collimated beams of diffracted coherent light impinging on a detector of a system for detecting the diffracted coherent light.

According to a further aspect of such device, the straight parallel lines of at least one spatially separated area of the plurality of spatially separated areas include a first angle $\beta_1$ with the predetermined propagation direction of the coherent light in the planar waveguide, and wherein the straight parallel lines of at least one other spatially separated area of the plurality of spatially separated areas include a second angle $\beta_2$ with the predetermined propagation direction of the coherent light in the planar waveguide, wherein the first angle $\beta_1$ is different from the second angle $\beta_2$.

A device with at least two spatially separated areas having the straight parallel lines arranged at different angles $\beta_1$ and $\beta_2$ has the advantage that the collimated beams of diffracted coherent light propagating away from the respective spatially separated areas have different detection directions, especially different transversal angles $\gamma_1$ and $\gamma_2$. As will be discussed in more detail below, depending on the requirements of the system employed to detect the collimated beams of diffracted coherent light, the detection directions of the collimated beams of diffracted light can be configured such that the collimated beams of diffracted light impinge on the detector of the system either at larger or smaller distances than the distances of the spatially separated areas on the device. Or to say it in other words, it is possible to decouple the spacing of different areas of straight parallel lines on the device and the spatial spacing of different collimated beams of diffracted coherent light when impinging on a detector of a system for detecting the diffracted coherent light.

According to a further aspect of such device, at least one spatially separated area of the plurality of spatially separated areas has a first type of binding sites capable of binding a first type of target samples, and wherein at least one other spatially separated area of the plurality of spatially separated areas has a second type of binding sites capable of binding the first type of target samples or a second type of target samples, wherein the first type of binding sites is different from the second type of binding sites.

In many applications, it is desirable to know if a substance contains different types of target samples. Advantageously, the testing of the substance for the presence of different target samples can be done with a single device. Therefore, one single device may comprise a plurality of spatially separated areas with different spatially separated areas comprising different types of binding sites such that for each different type of target samples at least one spatially separated area exists comprising a type of binding sites capable of binding to said type of target samples. It is also possible to use different types of binding sites in different areas, wherein the different types of binding sites are capable of binding to identical types of target samples, e.g. for the purpose of checking the binding affinities of different types of binding sites to an identical type of target samples.

According to a further aspect of such device, the device comprises a plurality of spatially separated sections on the outer surface of the planar waveguide, each spatially separated section comprising one or more of said spatially separated areas and a said optical coupler.

Having a plurality of sections each comprising an optical coupler and one or more of such spatially separated areas provides for the opportunity to consecutively read out such sections one after the other with a suitable system. Therefore, further advantages of such a plurality of spatially spaced sections as well as the reading out of the sections become apparent when discussing the corresponding system aspects later on.

The size of a section may typically be between 1 mm$^2$ and 100 mm$^2$. However, the size of the section can be smaller or larger without departing from the scope of this invention. In total, up to 10000 spatially separated sections can be arranged on one device according to the invention. Advantageously, each section comprises more than 10 spatially separated areas. For best utilization of the space on a device, the shape of a section can be polygonal, rectangular or quadratic.

The intensity of the coherent light propagating in the predetermined propagation direction through the planar waveguide decreases during propagation. Therefore, the evanescent field also decreases in the predetermined propagation direction. For example, after a distance of 8 mm from the optical coupler the intensity of the evanescent field may have decreased to one third of the intensity at the optical coupler. Therefore, depending on the size of the spatially separated areas arranged in one section, preferably no more than 10 areas are placed one after another in a row in the predetermined propagation direction before a different section having its own optical coupler starts.

According to a further aspect, the optical coupler may comprise a grating. The term grating is intended to comprise both, a physical grating and a biological grating.

The grating may comprise equally spaced straight parallel physical or biological lines. Physical lines can be, for example, grooves, elongated protrusions or periodical changes of the refractive index of the planar waveguide. Biological lines can be formed by target samples bound to binding sites (however, these target samples bound to binding sites of the coupler are not to be mixed-up with the target samples that are intended to be bound to the binding sites arranged along the straight parallel lines for detection of the binding affinity).

According to a further aspect, such device may comprise a hydrogel layer arranged on the outer surface of the planar waveguide and covers the binding sites. The hydrogel layer is configured to allow the target samples to diffuse therethrough for allowing them to bind to the binding sites. The hydrogel layer is further configured to prevent molecules exceeding a predetermined size which is larger than the size of the target samples from diffusing therethrough.

According to a further aspect, in an area where the optical coupler is arranged a cover layer is arranged on the outer surface of the planar waveguide, the cover layer being transparent to light of the predetermined wavelength. An absorption layer is arranged on the transparent cover layer, the absorption layer being absorptive to light of the predetermined wavelength.

Any coherent light that is not coupled into the planar waveguide may possibly lead to stray light that may reach the array detector and would therefore falsify the measurement of the light diffracted at the target samples bound to the binding sites. To avoid such stray light, the absorption layer extincts such coherent light that has passed through the transparent layer to avoid that stray light that may possibly result from such non-coupled portions of impinging light may reach the array detector.

According to a further aspect, that outer surface of the planar waveguide opposite to the outer surface on which the binding sites are located (or arranged) is covered with an anti-reflection coating. Such anti-reflection coating, for example a λ/4 layer, further reduces reflections that may occur and that may also possibly lead to unwanted light at the array detector.

As mentioned, another aspect relates to a system for the detection of binding affinities. The system comprises such device as has been described above. Further, the system comprises a light source for emitting coherent light of a predetermined wavelength. The light source and the device are arranged relative to one another such that the coherent light emitted from the light source is coupled into the planar waveguide via the optical coupler of the device. In addition, the system comprises a lens for focusing the collimated beam of diffracted coherent light propagating away from the planar waveguide in a predetermined detection direction into a focal point. Also, the system comprises a detector positioned optically downstream of the lens in the focal point of the lens, for detecting the diffracted coherent light of the collimated beam focused into the focal point of the lens. Finally, the system comprises an evaluation device for providing a signal representative of the diffracted coherent light detected by the detector. The signal is indicative of the affinity of the target samples to bind to the binding sites.

In operation, coherent light which has been diffracted by target samples bound to binding sites arranged along the straight parallel lines on the outer surface of the planar waveguide can be detected in the focal point of the lens as a measure for the affinity of the target samples to bind to the biding sites. For example, the intensity or the amount of the diffracted coherent light provided at the focal point of the lens is detected and compared to a known intensity of coherent light which has been diffracted by the binding sites only, i.e. without target samples bound thereto, or by a physical grating on the outer surface of the planar waveguide.

The change in intensity or the amount of diffracted coherent light is representative of (i.e. is a measure for) the affinity of target samples to bind to the binding sites since the intensity or the amount of light at the focal point of the lens is significantly different when target samples have bound to the binding sites. This allows for the detection of target samples.

The light source can be a laser or a laser diode. In case of parallel coherent light being emitted from the light source, the diameter of said parallel beam may be 500 μm, for example.

The lens can be an optical lens. The aperture of the lens captures the amount of light focused in the focal point.

The detector may be an array detector. For example, the detector can be a CCD image sensor a CMOS image sensor or a time of flight image sensor, i.e. an array detector that incorporates time-of-flight discrimination of the detected light. The detector is positioned at the focal point of the lens and is arranged to extend perpendicular to the optical axis of the lens.

Providing a signal representative of the diffracted coherent light detected by the detector includes also displaying a signal which is representative of the diffracted coherent light detected by the detector.

No spectrometer is needed as no shift or change in the frequency spectrum of the coherent light occurs within the system. Also, no pinholes are necessary for blocking unwanted light.

In operation, there can be multiple collimated beams of diffracted coherent light at the same time, and the system is then suitable to detect multiple collimated beams of diffracted coherent light at the same time.

Due to the simplicity of such system, the system is especially suitable for a cost effective operation at the "point of care", i.e. at the point where the testing of a substance for the presence of target samples is most desirable and possible without the need to transport the substance possibly containing the target samples to a central laboratory.

According to one aspect of such system, the system further comprises a scanner and de-scanner being arranged in an optical path between the light source and the planar waveguide (proximate to the planar waveguide) for directing coherent light emitted from the light source towards the optical coupler in a manner such that the amount of the coherent light coupled into the planar waveguide is maximal.

The scanner and de-scanner is a device which is capable of both directing coherent light emitted from the light source towards the optical coupler and directing the collimated beam of diffracted coherent light propagating away from the planar waveguide, by deflecting both the coherent light emitted from the light source and the collimated beam of diffracted coherent light propagating away from the planar waveguide in the same manner.

The advantage of such a scanner and de-scanner is that in case the device according to the invention is not positioned in the system exactly as intended but at a certain unwanted inclination, the scanner and de-scanner is capable to correct for such an unwanted inclination and therefore ensures that there will be no detection error caused by any unwanted inclination of the device.

The scanner and de-scanner is arranged proximate to the planar waveguide at a working-distance from the planar waveguide in the range of some mm (millimeters) up to about 1 cm or even 10 cm (centimeters). The maximum possible working distance depends on the diameter of the collimated beam of diffracted coherent light propagating away from the planar waveguide in the predetermined detection direction and the aperture of the lens. For example, for a spatially separated area with a diameter of 20 μm (micrometers) and comprising about 60 straight parallel lines, the working-distance may be 1 mm. For a spatially separated area with a diameter of 1 mm and comprising about 3000 straight parallel lines, the working distance may be 5 cm. In any case, the working distance of such system is much larger than any working distance of a prior art system using planar waveguides and diffracted light to determine binding affinities.

According to a further aspect of such system, the system comprises a mirror. The mirror has a front surface configured to reflect the collimated beam of diffracted coherent light towards the lens. The rear surface of the mirror is configured to allow the coherent light emitted from the light source to pass through the mirror. The mirror is arranged in an optical path of the diffracted coherent light between the scanner and de-scanner and the lens and in an optical path of the coherent light between the light source and the scanner and de-scanner.

The mirror may increase the detection accuracy as less scattered light may impinge on the detector. Further, the mirror allows for a more compact constructional design of the detection system.

According to a further aspect of such system, the scanner and de-scanner may comprise a pivotable mirror and a telescopic lens arrangement. The telescopic lens arrangement has two further lenses arranged in an optical path of the diffracted coherent light between the planar waveguide and the pivotable mirror. The system further comprises an additional mirror arranged in an optical path of the coherent light emitted from the light source between the light source and the pivotable mirror. The additional mirror is configured to reflect the coherent light emitted from the light source, and is further configured to allow the collimated beam of diffracted coherent light to pass through the additional mirror.

The pivotable mirror or the pivotable mirror together with the telescopic lens arrangement can be embodied in form of a MEMS (microelectromechanical system). A typical size of such a mirror can be 2 mm×2 mm. For example, the mirror can be pivoted by 1°-2° through voltage-control.

According to yet a further aspect of such system, the system further comprises an actuator for consecutively positioning the optical coupler of each spatially separated section of the plurality of spatially separated sections of the device in the path of the coherent light emitted from the light source such that the coherent light emitted from the light source is consecutively coupled into the planar waveguide at the respective spatially separated section.

The actuator for consecutively positioning the optical coupler of each spatially separated section provides the opportunity to consecutively "read out" the respective sections. "Read out" means to detect the diffracted coherent light propagating away from the spatially separated areas of a particular section in form of multiple collimated beams at the respective focal points.

The actuator can be controlled to read out a specific number of sections or all sections in a predetermined manner.

According to a further aspect of such system, the system further comprises at least one magnet which is movably arranged for being positioned at the side of the planar waveguide in close proximity to the binding sites or in a distant position to the binding sites. In a preferred embodiment the magnet is placed at a first position on a side of the planar waveguide opposite to the side where the binding sites are arranged on the planar waveguide, or at a second position on the same side of the planar waveguide where the binding sites are arranged on the planar waveguide, or at a third position in which the magnet is arranged out of the path of the coherent light from the light source to the optical coupler of the planar waveguide as well as out of the path of the collimated beam of diffracted coherent light from the planar waveguide to the detector.

This embodiment is advantageous in that magnetically labelled target samples can be moved to the binding sites more rapidly. With the magnet being arranged in the first position, the magnetically labelled target samples are moved to the binding sites with the aid of the magnetic field where they possibly bind to the binding sites. Subsequently, target samples not bound to the binding sites are removed by arranging the magnet in the second position. Thereafter, the magnet is removed out of the path of any light in order to allow for detection of the binding affinity. Transportation of magnetically labelled samples is described, for example, in the article "Rapid integrated biosensor for multiplexed immunoassays based on actuated magnetic nanoparticles" by D. M. Bruls et. al., published in the journal "The Royal Society of Chemistry", 2009, 9, page 3504-3510.

BRIEF DESCRIPTION OF THE DRAWINGS

Further advantageous aspects of the invention become apparent from the following description of embodiments of the invention with reference to the accompanying schematic drawings in which.

DETAILED DESCRIPTION

Figure 3:
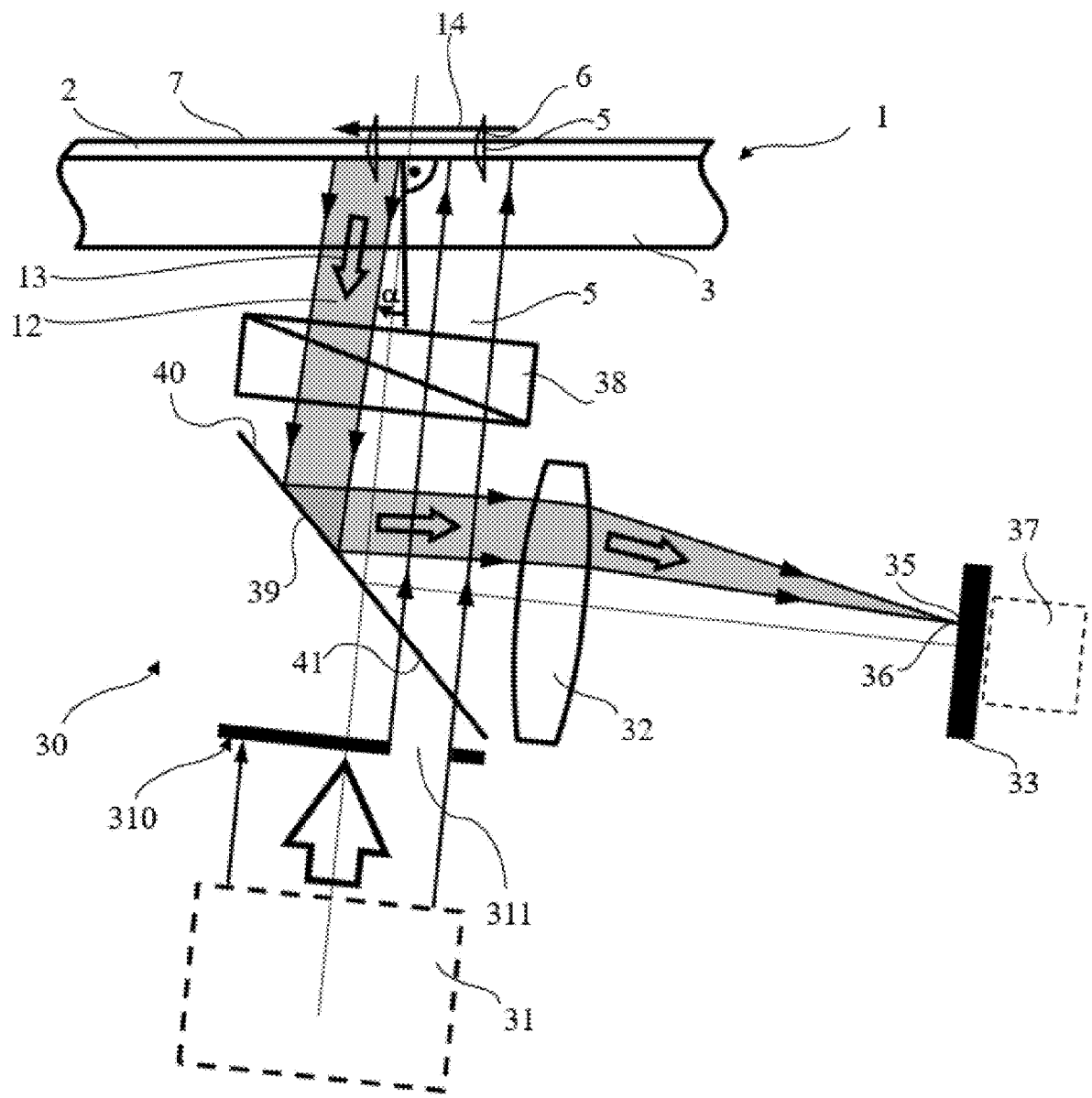
FIG. 3 shows a first embodiment of the system according to the invention.

A first embodiment of a device 1 according to the invention will be explained with the aid of FIG. 1 and FIG. 3. As can be seen in FIG. 3, a planar waveguide 2 is arranged on top of substrate 3 and comprises outer surface 7 at the upper side of planar waveguide 2 opposite to the substrate 3. Outer surface 7 of planar waveguide 2 comprises a plurality of straight parallel lines 11 arranged within a plurality of spatially separated decouplers 20, as can be seen best in FIG. 1. A plurality of receptor molecules 8 are arranged along the plurality of straight parallel lines 11. Between the straight parallel lines 11 along which the receptor molecules 8 are arranged interstices 110 are formed, and in these interstices filler molecules 80 are arranged. As has already been discussed further above, the filler molecules 80 can be identical with the receptor molecules 8 except that they are deactivated. Accordingly, while the receptor molecules 8 are capable of binding target samples 9 to the receptor molecules 8, the filler molecules 80 are incapable of binding the target samples 9 to the filler molecules 80 due to being deactivated. Together, the receptor molecules 8 arranged along the straight parallel lines 11 and the filler molecules 80 arranged in the interstices 110 between these straight parallel lines 11 form an optically smooth area, as has been explained further above already.

The adjacent straight parallel lines 11 of the respective decouplers 20 are arranged at a distance d from each other which is measured in the predetermined propagation direction 14 of the coherent light in the planar waveguide, and this propagation direction corresponds to the direction of the length 200 (see FIG. 2) of the planar waveguide. In the embodiment shown in FIG. 1, the distance d between the straight parallel lines at each separated decoupler 20 is constant (although this is not a must) and may be an integer multiple of a minimum distance $d_{min}$ between adjacently arranged straight parallel lines 11. The minimum distance $d_{min}$ can be calculated as has been described further above. Different decouplers 20 can have different distances d, for example, the distance d between adjacent straight lines 11 of the lowermost decoupler 20 shown in FIG. 1 may be $d_2$ whereas the distance d between adjacent straight lines in the second decoupler 20 from the top may be $d_1$. A longitudinal angle α (FIG. 3) between a collimated beam 12 of diffracted coherent light and a normal to outer surface 7 of planar waveguide 2 is determined by the minimum distance $d_{min}$ between the adjacently arranged straight parallel lines 11 (given the predetermined wavelength of the coherent light).

Figure 1:
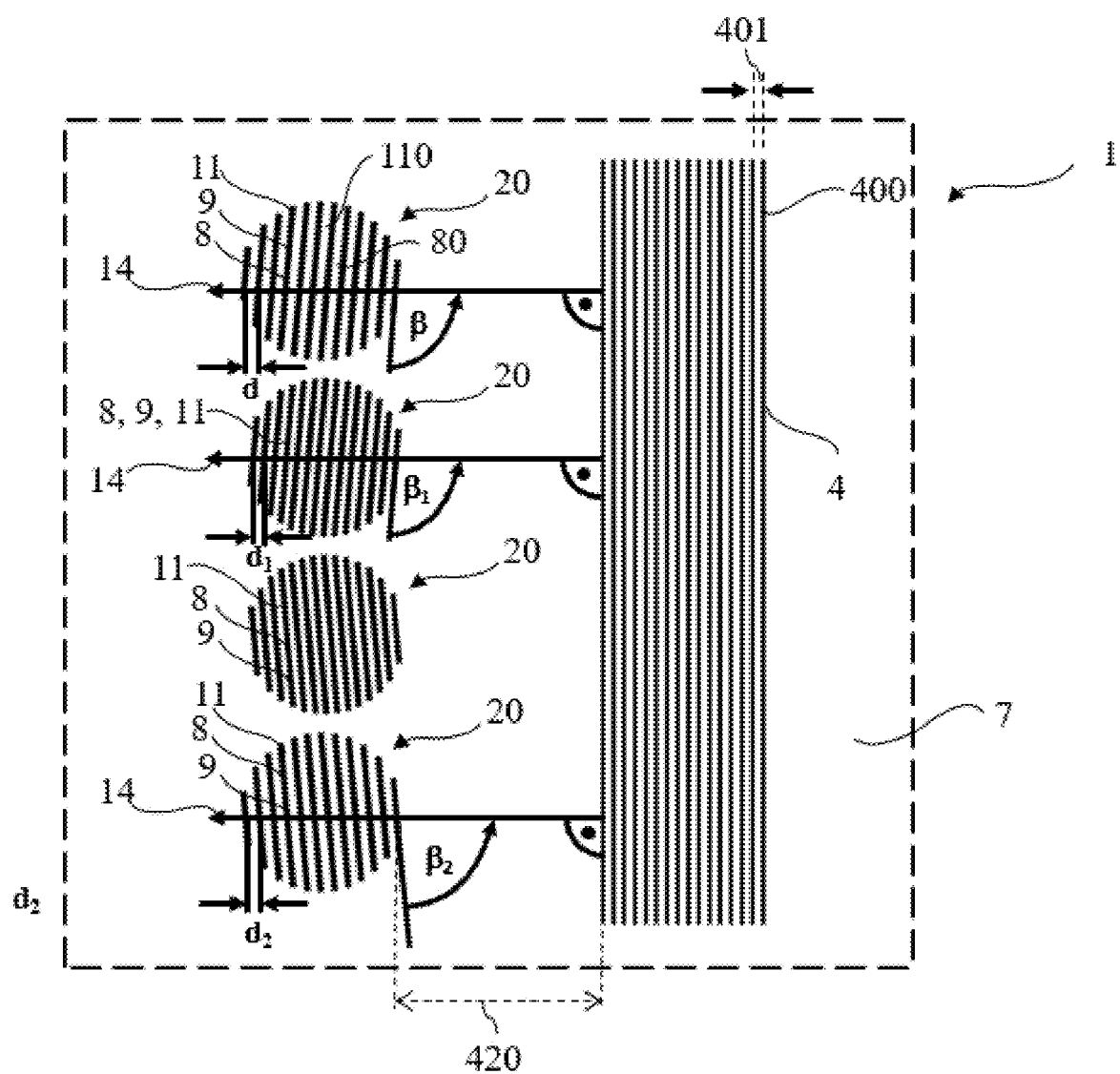
FIG. 1 shows a top view of a portion of a first embodiment of the device according to the invention.

As can be seen from FIG. 1, device 1 further comprises a grating 4 comprising a plurality of straight, equally spaced grating lines 400 extending in the direction of the width 201 (see FIG. 2) of the planar waveguide and having a grating period 401 in the direction of the length 200 (see FIG. 2) of the planar waveguide. Grating period 401 is less than 1 µm (micrometer). The grating lines 400 can be embodied as grooves (not shown) at the outer surface of the planar waveguide 2 which is arranged on and supported by the substrate 3. The coupling of a parallel beam of coherent light 5 coming from a laser light source 31 into planar waveguide 2 is performed with the aid of grating 4 (FIG. 1) and causes the parallel beam of coherent light 5 to propagate through planar waveguide 2 in the predetermined propagation direction 14 (which corresponds to the direction of the length 200 of the planar waveguide, see FIG. 2), with an evanescent field 6 of the parallel beam of coherent light 5 propagating along the outer surface 7 of the planar waveguide 2 (FIG. 3).

Each of the decouplers 20 is arranged spaced apart from the grating 4 by a distance 420 of at least 10 µm (micrometers). The decouplers 20 each comprise a plurality of straight parallel lines 11 along which the receptor molecules 8 are attached to the outer surface 7 of the planar waveguide 2. In operation, target samples 9 are applied to outer surface 7 of planar waveguide 2 and are bound to the receptor molecules 8 (in case of a binding affinity between the target samples 9 and the receptor molecules 8) whereas no target samples 9 are bound to the filler molecules 80.

The distance d (or $d_1$, $d_2$, respectively) between adjacently arranged straight parallel lines 11 and the angle β between the straight parallel lines 11 and the predetermined propagation direction 14 are chosen such that a portion of the coherent light of the evanescent field 6 is diffracted at the target samples 9 bound to the receptor molecules 8 such that a collimated beam 12 of the diffracted coherent light propagates away from planar waveguide 2 (see FIG. 3) in the predetermined detection direction 13 (represented by the arrow). The angle β between the straight parallel lines 11 and the predetermined propagation direction 14 can preferably be chosen from the range that has been described further above (i.e. from a range between 60° and 120°, preferably between 75° and 105°).

The collimated beam 12 of diffracted coherent light in this first embodiment is a parallel beam of coherent light but may also be slightly diverging, as is explained further below. Additional optical elements, for example a lens 32 (see FIG. 3) which is not part of device 1 per se but is an element of the system 30, is required to focus collimated beam 12 of diffracted coherent light into focal point 35. Therefore, the position of focal point 35 is not determined by the device 1 itself but rather is determined by the system 30. Predetermined detection direction 13 is defined by longitudinal angle α and transversal angle γ (not shown), which is an angle between the predetermined detection direction and a plane extending through both a normal to the outer surface 7 of the planar waveguide 2 and the predetermined propagation direction 14 of the coherent light in the planar waveguide (i.e. between the predetermined detection direction 13 and a plane corresponding to the plane of the drawing of FIG. 3).

As already mentioned, the size of the spatially separated decouplers 20 can be very small. Advantageously, several spatially separated decouplers 20 with receptor molecules 8 arranged along the straight parallel lines 11 of the respective decouplers 20 are arranged on device 1. This allows for simultaneous multiple detection of binding affinities. Multiple collimated beams 12 of diffracted light propagate away from planar waveguide 2 in predetermined detection directions 13 simultaneously. The distance d between the straight parallel lines 11 and the angle β of each individual spatially separated decoupler 20 can be configured such that each collimated beam 12 has a desired predetermined detection direction 13. The respective desired predetermined detection direction 13 can be chosen such that each focal point 35 is arranged at a desired position on array detector 33. Such a zone comprising a plurality of spatially separated decouplers 20 and a grating 4 is in the following called a section 25. One or more such sections 25 may be arranged on a device according to the invention (see FIG. 2).

Figure 2:
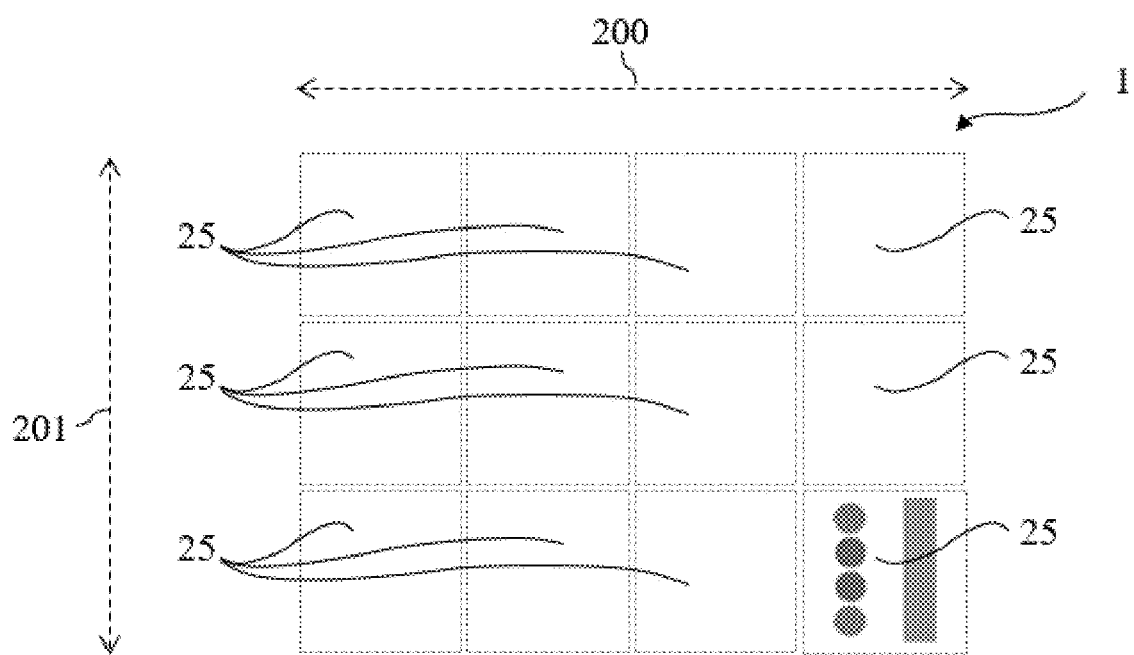
FIG. 2 shows a top view of a portion of a second embodiment of the device according to the invention.

FIG. 2 shows a second embodiment of a device 1 according to the invention. Device 1 comprises a plurality of the afore-described sections 25. By way of example, one such section 25 shown at the lower right end in FIG. 2 (similar to that of FIG. 1) explicitly shows the features of such section 25. The other sections 25 are indicated only schematically in FIG. 2 without showing any detailed features. These sections 25 can be identical with the section 25 shown at the lower right end in FIG. 2 or can be different. In the second embodiment of the device 1 according to the invention as shown in FIG. 2, the sections 25 are arranged in a symmetric and periodic manner. Also indicated in FIG. 2 are the direction of the width 201 and the direction of the length 200 of the planar waveguide (dashed double-headed arrows).

FIG. 3 shows a first embodiment of the system 30 for detecting binding affinities according to the invention.

In this first embodiment, system 30 comprises a laser light source 31 which emits a parallel beam of coherent light 5 having a predetermined wavelength. A diaphragm 310 can be arranged in the path of the beam of coherent light 5 emitted by the laser light source 31, and this diaphragm 310 may comprise one or more transparent sections 311 which selectively allow the coherent light 5 to pass through the respective transparent section or sections 311 of the diaphragm 310. By this measure, it is possible to selectively direct the coherent light 5 emitted by the laser light source 31 either to a selected one or to a selected plurality of the different sections 25 (see FIG. 2) at the same time. It is thus possible to sequentially scan the individual sections 25 by allowing the coherent light 5 emitted by the laser light source 31 to pass through the respective transparent sections 311 one after the other (while the respective other transparent sections 311 are shut), so that the individual sections 25 on the planar waveguide 2 are read out one after the other. Alternatively, it is possible to read out a selected plurality of sections 25 at the same time by allowing the coherent light 5 emitted by the laser light source 31 to pass through a corresponding plurality of transparent sections 311 of the diaphragm 310 at the same time. Although this would generally allow for all sections 25 on the planar waveguide 2 to be read out at the same time, this may increase the amount of background light and may lead to a reduced signal-to-noise ratio. System 30 further comprises a mirror 39, the rear surface 41 of which is transparent for the coherent light 5, and a scanner and de-scanner 38. The parallel beam of coherent light 5 travels through the scanner of scanner and de-scanner 38 to impinge on grating 4 (see FIG. 1) in a manner such that the coherent light is optimally coupled into planar waveguide 2 to thereafter propagate through the planar waveguide 2 in the predetermined propagation direction 14. In case the substrate 3 with the planar waveguide 2 arranged thereon is not arranged as shown in FIG. 3—for example substrate 2 with planar waveguide 2 arranged thereon is arranged slightly inclined relative to the position shown in FIG. 3—this inclination is compensated for by the scanner of scanner and de-scanner 38 which slightly deflects the beam of coherent light 5. As a consequence, the beam of coherent light 5 is optimally coupled into planar waveguide 2 to propagate therethrough. In case of such inclination of the substrate 3 with the planar waveguide 2 arranged thereon, the collimated beam 12 of diffracted coherent light (diffraction caused by the target samples bound to the binding sites) also propagates in a detection direction which slightly deviates from the detection direction 13 shown in FIG. 3. This deviation is compensated for by the de-scanner of scanner and de-scanner 38 which deflects the diffracted coherent light such that it propagates again in the detection direction 13. In total, the scanner and de-scanner 38 compensates for minor improper arrangements of the substrate 3 with the planar waveguide 2 arranged thereon. After having passed through scanner and de-scanner 38, the collimated beam of diffracted light propagates away from the planar waveguide 2 of device 1 in the predetermined detection direction 13, as has already been explained above, and impinges onto the front surface 40 of mirror 39 which is reflective for the diffracted coherent light. In the further optical path, the diffracted coherent light reflected by mirror 39 impinges onto focusing lens 32 which generates a focused collimated beam 36 at focal location 35 on array detector 33. Evaluation device 37 generates a signal which is representative of the light detected by array detector 33 at focal location 35 and is thus indicative of the affinity of the target samples 9 to bind to the receptor molecules 8.

Figure 4:
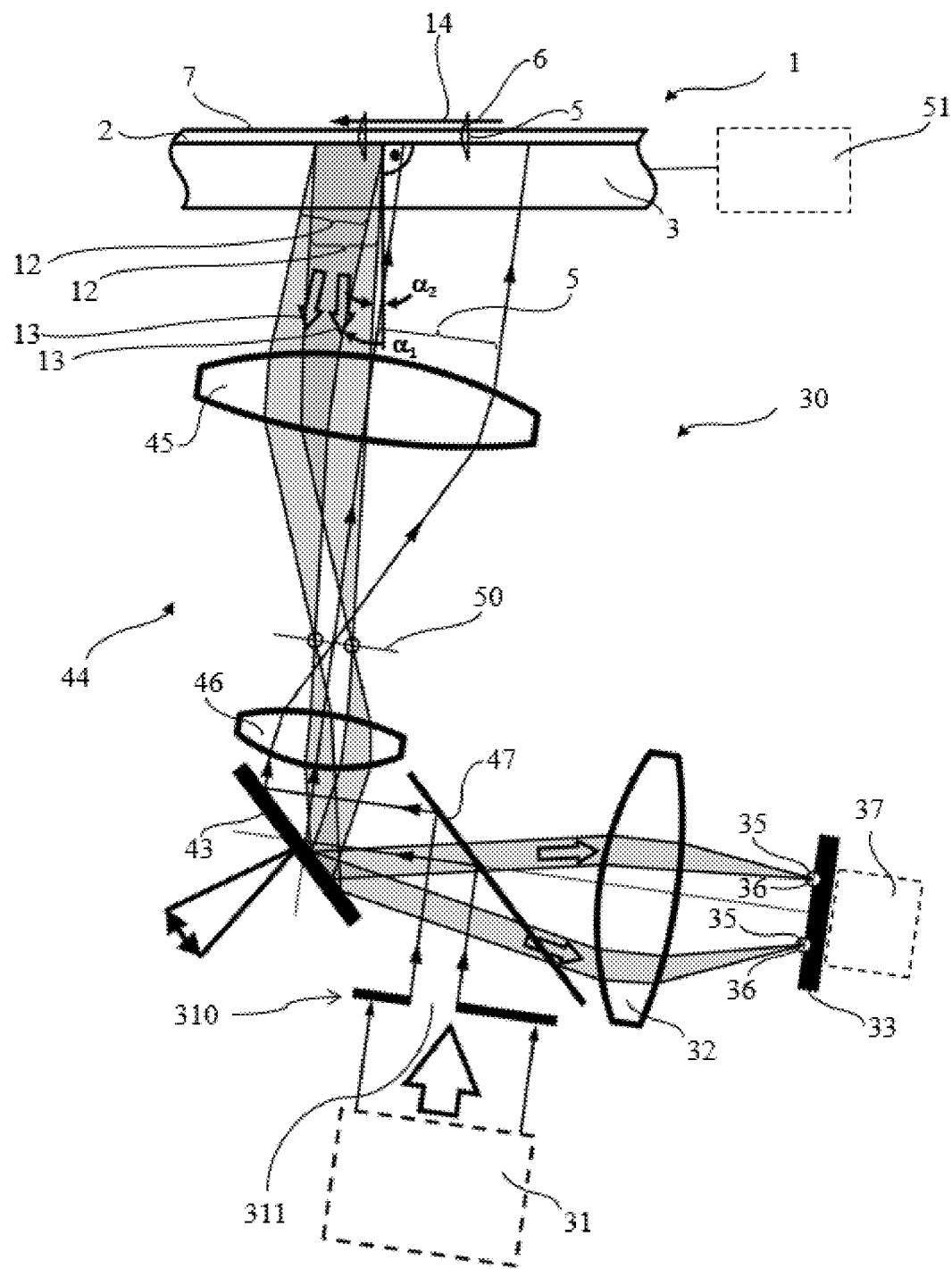
FIG. 4 shows a second embodiment of the system according to the invention.

FIG. 4 shows a second embodiment of the system 30 for detecting binding affinities according to the invention. The scanner and de-scanner 38 shown in FIG. 3 is formed by pivotable mirror 43 and a telescopic lens arrangement 44 comprising two further lenses 45, 46. Additionally, the mirror 39 shown in FIG. 3 is formed by further mirror 47 and pivotable mirror 43 in this second embodiment of the system 30. Again, a diaphragm 310 can be arranged in the path of the beam of coherent light 5 emitted by the laser light source 31, and this diaphragm 310 may again comprise one or more transparent sections 311 which selectively allow the coherent light 5 to pass through the respective transparent section or sections 311 of the diaphragm 310 similar to FIG. 3 above, so that the mode of operation of the diaphragm 310 is not explained again here. The parallel beam of coherent light 5 emitted from laser light source 31 is reflected by fixedly arranged further mirror 47 towards pivotable mirror 43. Pivotable mirror 43 reflects the parallel beam of coherent light 5 emitted from laser light source 31 towards further lens 46 and then towards further lens 45 in a manner such that the coherent light 5 coupled into planar waveguide 2 by grating 4 (see FIG. 1) is maximal. In more detail, the parallel beam of coherent light 5 reflected by pivotable mirror 43 passes through further lens 46 of telescopic lens arrangement 44 and is focused in a virtual focal plane 50 from which it divergently propagates towards further lens 45 of the telescopic lens arrangement 44. Further lens 45 forms a parallel beam of coherent light 5 which impinges on grating 4 of planar waveguide 2.

Light of the evanescent field 6 is diffracted by target samples 9 bound to receptor molecules 8 which are arranged on outer surface 7 of planar waveguide 2 in four spatially separated decouplers 20 along the straight parallel lines 11 (see FIG. 1). Accordingly, four collimated beams 12 of diffracted coherent light, one collimated beam from each spatially separated decoupler 20, are propagating away from planar waveguide 2 in predetermined detection directions 13. As can be seen from FIG. 1, two of the spatially separated decouplers 20 have the same distance d between adjacently arranged straight parallel lines 11 (the two outer decouplers, i.e. the uppermost and lowermost decoupler, and the two inner decouplers, respectively), and two spatially separated decouplers 20 have the same angle β between adjacently arranged straight parallel lines 11 and the predetermined propagation direction 14 of coherent light 5 in the planar waveguide 2 (the two lower decouplers and the two upper decouplers, respectively). Therefore, two collimated beams 12 have the same longitudinal angle $\alpha_1$ (propagating away from the two outer areas and the two inner areas, respectively) and two collimated beams have the same transversal angle γ (propagating away from the two lower decouplers and the two upper decouplers, respectively). As FIG. 4 cannot separately show collimated beams 12 with different transversal angles γ, only collimated beams 12 having different longitudinal angles $\alpha_1$, $\alpha_2$ are shown separately. The four collimated beams 12 are focused by further lens 45 of telescopic lens arrangement 44 in focal plane 50, from where the beams divergently propagate to further lens 46 of telescopic lens arrangement 44. Further lens 46 of telescopic lens arrangement 44 again forms collimated beams 12 of diffracted coherent light. Pivotable mirror 43 reflects these collimated beams 12 towards fixedly arranged mirror 47 which is transparent for the respective angles of impingement of the collimated beams of diffracted light, so that the collimated beams 12 pass through mirror 47 and impinge on lens 32 which forms focused collimated beams at four different focal points 35 on the array detector 33.

Figure 5:
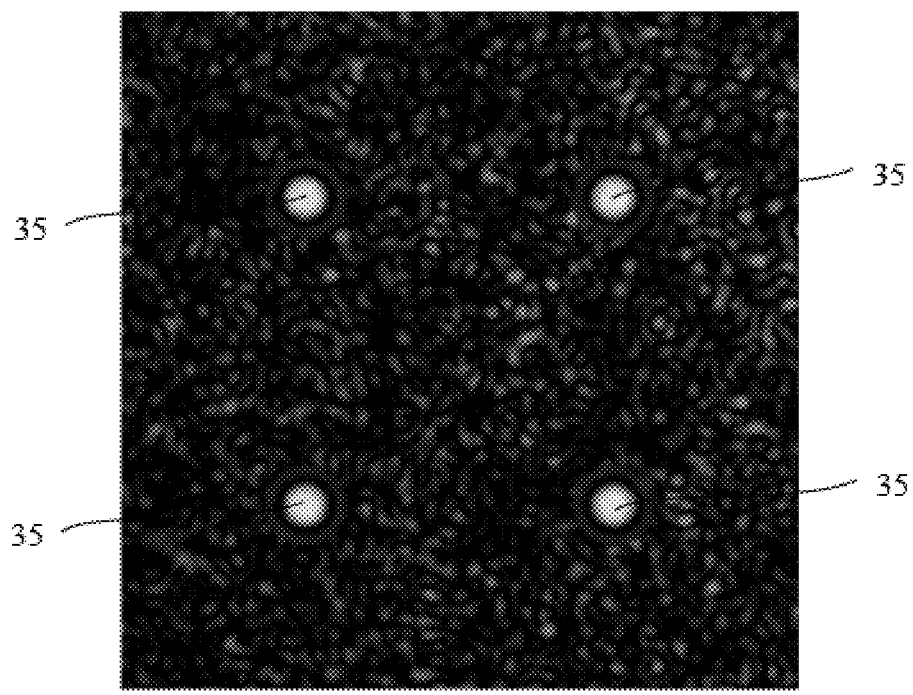
FIG. 5 shows an embodiment of an image detected by the detector.

An image of the diffracted coherent light at the four focal points 35 on the array detector 33 is schematically shown in FIG. 5.

Returning to FIG. 4, evaluation device 37 generates a signal representative of the diffracted coherent light detected by array detector 33 at the respective focal point. This signal is indicative of the affinity of the target samples 9 to bind to the respective receptor molecules 8.

As is indicated in FIG. 4 by dashed lines, system 30 further comprises actuator 51 for moving device 1. In case the device comprises a plurality of individual sections 25 (see FIG. 2), these sections 25 of device 1 can be read out consecutively.

As has already been mentioned, FIG. 5 shows a schematic image of the diffracted coherent light at the four focal locations 35 on the array detector 33. Each of the four focused collimated beams 36 forms a bright area at the respective focal point 35. To increase the intensity or amount of diffracted coherent light, nanoparticles binding to target samples 9 which bind to receptor molecules 8 can be used to form a sandwich-structure. In general, nanoparticles and/or sandwich-structures of receptor molecules 8 can be used in any embodiment of the invention as such sandwich-structures strongly diffract coherent light and therefore lead to a very reliable determination of the binding affinities.

The image shown in FIG. 5 is otherwise basically dark, except for the little speckles symbolizing scattered incoherent background light (the intensity is by far lower than the intensity at the pronounced focal points 35).

Figure 6:
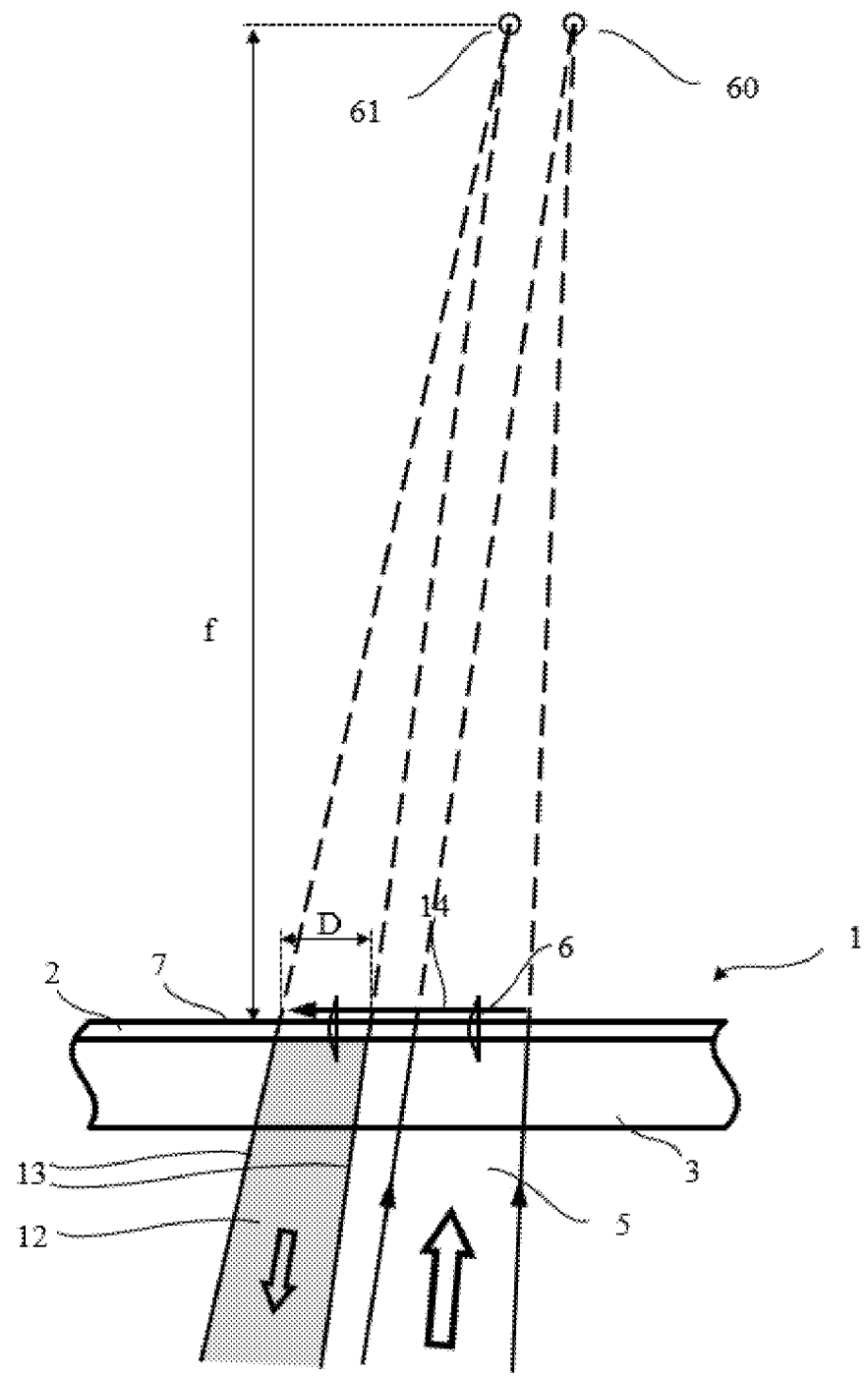
FIG. 6 shows a third embodiment of the device according to the invention configured to cause a slightly diverging beam of diffracted coherent light.

FIG. 6 shows device 1 operated with a slightly diverging collimated beam 12 of diffracted coherent light (divergence shown exaggerated). In this case, the device 1 is exposed to coherent light 5 coming from the light source and propagating towards the grating 4 of the planar waveguide 2 forming a slightly converging beam. The dashed lines on the right side of FIG. 6 represent a virtual path of the coherent light 5 in case it was not coupled into the planar waveguide 2 but would continue to propagate through device 1 and converge into virtual focal point 60. The dashed lines on the left side of FIG. 6 end in a virtual focal point 61 where the collimated (slightly diverging) beam of diffracted coherent light virtually comes from. The diameter D of the slightly diverging collimated beam 12, measured at the outer surface 7 of planar waveguide 2, is small compared to the focal length f of virtual focal point 61.

Figure 7:
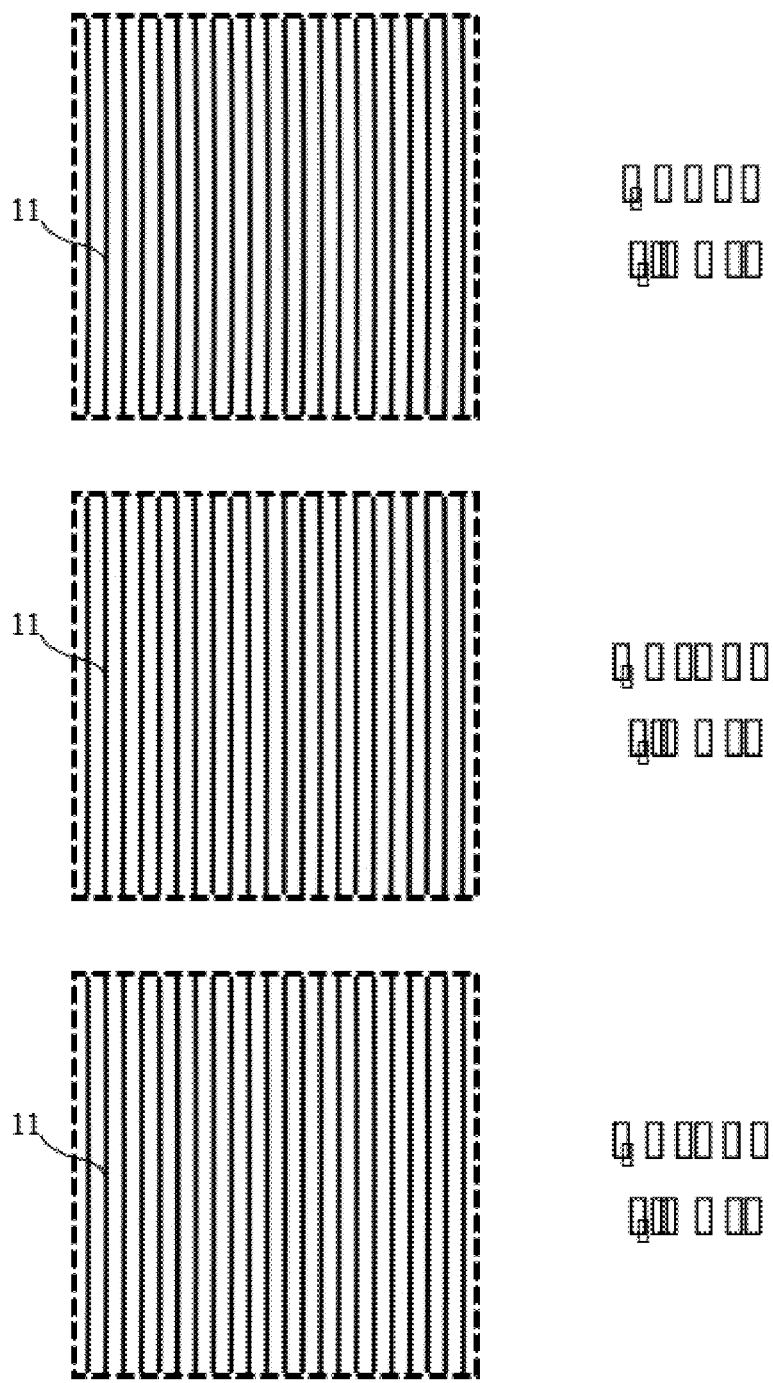
FIG. 7 shows a top view of a portion of the third embodiment of the device according to the invention with three different arrangements of the straight parallel lines for different ratios of f/D.

FIG. 7 shows examples of straight parallel lines 11 for three different virtual focal lengths $f_1$, $f_2$ and $f_3$ resulting in three different ratios $f_1/D$, $f_2/D$ and $f_3/D$.

Figure 8:
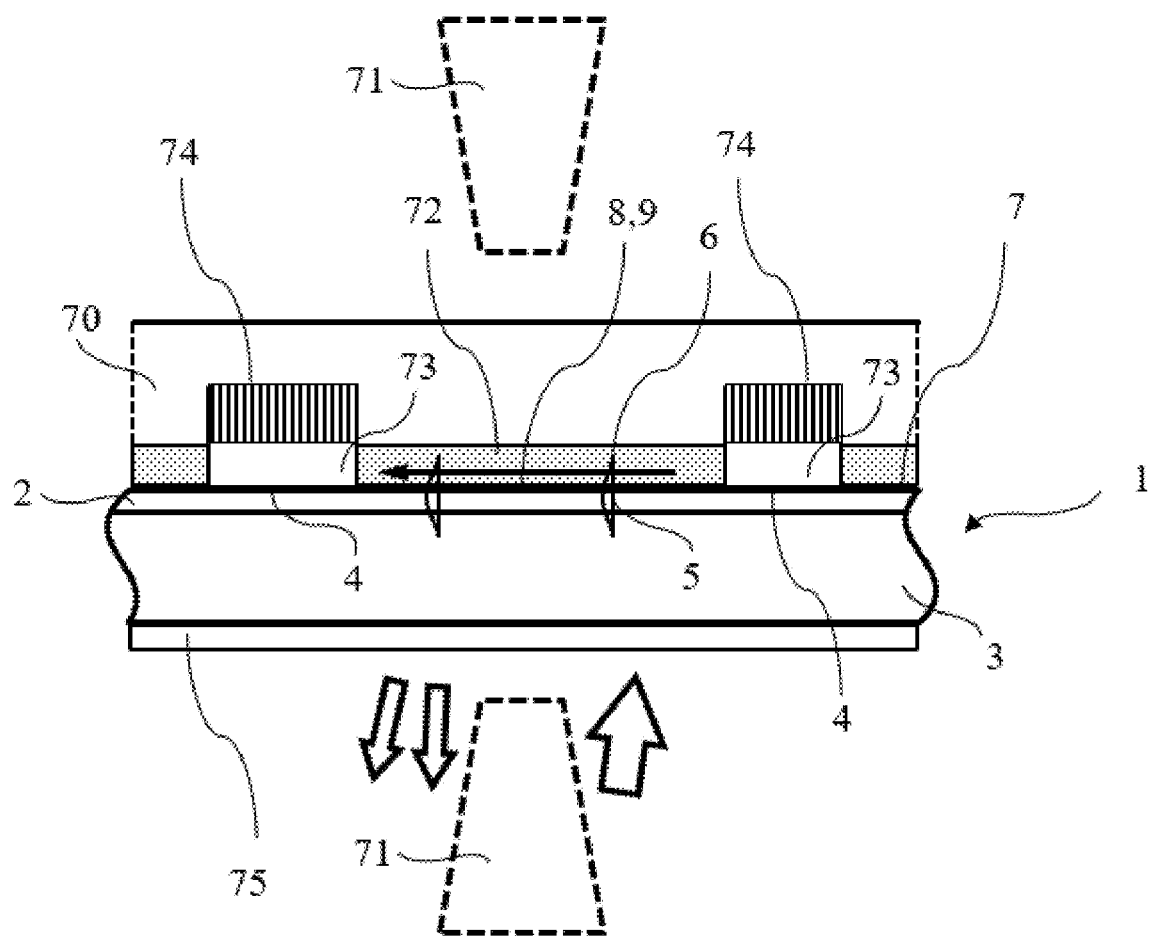
FIG. 8 shows a third embodiment of the system according to the invention comprising a magnet.

FIG. 8 shows a fluidic capillary gap 70 on the outer surface 7 of the planar waveguide 2 as well as a hydrogel layer 72 arranged on the outer surface 7 of the planar waveguide 2. The hydrogel layer 72 covers the outer surface 7 of the planar waveguide including the receptor molecules 8. In operation, the evanescent field 6 does not extend beyond the hydrogel layer 72. While target samples 9 may diffuse through the hydrogel layer 72 to bind to the receptor molecules 8, molecules exceeding a predetermined size larger than the size of the target samples 9 are prevented from diffusing therethrough. The hydrogel layer 72 thus functions as a screen keeping larger molecules away from the outer surface 7 of the planar waveguide 2 (and thus away from the receptor molecules 8 arranged thereon).

In addition, FIG. 8 shows a magnet 71 positioned at a first position beneath the planar waveguide 2 or at a second position above the outer surface 7 of planar waveguide 2. The first and second positions both correspond to the position of the decoupler 20. This is advantageous, for example, in cases in which a sample liquid containing magnetic labels, such as paramagnetic or supra-paramagnetic nanoparticles typically having a diameter of smaller than 150 nm, as well as containing target samples 9 is applied to the hydrogel layer 72. Typically, in such sample liquid the number of magnetic labels largely exceeds the number of target samples 9, so that only some of the nanoparticles have bound to the target samples 9 to form magnetically labelled target samples 9 while the vast majority of the nanoparticles are not bound to target samples 9. If this sample liquid is then applied to the hydrogel layer 72 it would take considerable time until the magnetically labelled target samples 9 reach the receptor molecules 8 arranged on the outer surface 7 of the planar waveguide 2. To accelerate this movement of the magnetically labelled target samples towards the receptor molecules 8, the magnet 71 is now positioned at the first position beneath the planar waveguide 2 and the magnetic field exerts a force on the magnetically labelled target samples 9 rapidly moving the magnetically labelled target samples 9 to the receptor molecules 8 so as to form an immuno-sandwich. The immuno-sandwich technology is well-known and significantly reduces the risk of erroneously binding target samples 9 to receptor molecules 8. At the same time, however, those magnetic nanoparticles that have not bound to target samples 9 are also moved towards the outer surface 7 of the planar waveguide 2 and may lead to reflections of the coherent light (or the evanescent field, respectively) that may not allow for the determination of binding affinities anymore. Accordingly, such non-bound magnetic nanoparticles as well as any magnetically labelled target samples 9 that have not bound to receptor molecules 8 must be removed from the outer surface 7 of the planar waveguide 2 before detection of the binding affinity may start. To remove these nanoparticles and any magnetically labelled target samples 9 that have not bound to receptor molecules 8 from the outer surface 7 of the planar waveguide 2, the magnet 71 is subsequently positioned in the second position above the planar waveguide 2. Permanent magnets may preferably be used. Electromagnets can be used as well, but as electromagnets have a relatively high current consumption, especially for handheld devices permanent magnets may be preferred. Once binding of target samples 9 to the receptor molecules 8 and removal of excess nanoparticles and non-bound magnetically labelled target samples 9 from the outer surface 7 of planar waveguide 2 has been completed, the magnet 71 can be moved to a third position where the magnet 71 is arranged remote from the path of the coherent light from the light source to the grating 4 of the planar waveguide 2 as well as remote from the path of the collimated beam of diffracted coherent light from the planar waveguide 2 to the detector, in order to not affect the detection of the binding affinities. As can also be seen in FIG. 8, a transparent cover layer 73 may be arranged on the outer surface at the locations where the gratings 4 for coupling light into or out of the planar waveguide 2 are arranged. Let us assume that the coherent light 5 coming from the laser light source 31 (see FIG. 3, FIG. 4) impinges on the grating 4 at the right hand side in FIG. 8, so that the coherent light 5 coupled into the planar waveguide 2 (see FIG. 3, FIG. 4) propagates in the predetermined propagation direction shown by the arrow in FIG. 8, with the evanescent field 6 of the coherent light propagating in the hydrogel layer 72 and partially being diffracted at the target samples 9 bound to the receptor molecules 8 arranged on the outer surface 7 of the planar waveguide 2 along the straight parallel lines 11 (see FIG. 1) of the decoupler 20. The coherent light diffracted at the target samples 9 bound to the receptor molecules 8 is detected as described above, whereas the coherent light 5 not diffracted at the target samples 9 bound to the receptor molecules 8 continues to travel along the planar waveguide 2 until it reaches the grating 4 arranged at the left hand side in FIG. 8 that decouples the non-diffracted coherent light out of the planar waveguide 2. A transparent cover layer 73 (e.g. a transparent silicon dioxide layer, $SiO_2$) may cover the outer surface 7 of the planar waveguide 2 at the locations where the gratings 4 are arranged, and this transparent cover layer 73 is itself covered by an absorption layer 74. Any coherent light 5 that is not coupled into the planar waveguide 2 may possibly lead to stray light that may reach the array detector 33 (see FIG. 3, FIG. 4) and would falsify the measurement of the light diffracted at the target samples 9 bound to the receptor molecules 8. To avoid such stray light, the absorption layer 74 extincts (absorbs) any coherent light that has passed through the transparent layer 73 to avoid that stray light that may possibly result from such portions of the coherent light may reach the array detector 33. In addition, that surface of the planar waveguide 2 opposite to the surface on which the receptor molecules 8 are arranged may be covered with an anti-reflection coating 75, for example a $\lambda/4$-layer, for the reduction of reflections that may occur and that may otherwise also possibly lead to unwanted light at the array detector 33.

Embodiments of the invention have been described with the aid of the drawings. However, the invention is not intended to be limited to these embodiments. Rather, various changes and modifications can be made without departing from the teaching underlying the instant invention. Therefore, the scope of protection is defined only by the appended claims.

The invention claimed is:

1. A device for use in the detection of binding affinities, the device comprising
    a substrate and a leakproof planar waveguide arranged thereon, the planar waveguide having a refractive index higher than the refractive index of the substrate, as well as a length and a width and an outer surface opposite to the substrate on which the planar waveguide is arranged,
    a grating arranged on the planar waveguide, the grating comprising grating lines extending in the direction of the width of the planar waveguide with a grating period in the direction of the length of the planar waveguide which is less than 1 micrometer, for in operation coupling coherent light of a predetermined wavelength incident on the grating into the planar waveguide such that the coherent light coupled into the planar waveguide propagates through the planar waveguide in a predetermined propagation direction that corresponds to the direction of the length of the planar waveguide, with an evanescent field of the coherent light propagating along the outer surface of the planar waveguide,
    a decoupler arranged on the outer surface of the planar waveguide spaced apart from the grating in the predetermined propagation direction by a distance of at least 10 micrometers,
        wherein the decoupler on the outer surface of the planar waveguide comprises receptor molecules arranged on the outer surface of the planar waveguide, the receptor molecules being capable of binding target samples to the receptor molecules, wherein the receptor molecules are arranged along a plurality of straight parallel lines which are spaced from each other such that in operation a portion of the coherent light of the evanescent field diffracted by the target samples bound to the receptor molecules is decoupled from the planar waveguide as a collimated beam of diffracted coherent light propagating away from the planar waveguide in a predetermined detection direction,
        wherein the decoupler on the outer surface of the planar waveguide further comprises filler molecules arranged on the outer surface of the planar waveguide in interstices formed between the straight parallel lines along which the receptor molecules are arranged, the filler molecules being incapable of binding the target samples to the filler molecules,
        and wherein the receptor molecules arranged along the predetermined straight lines and the filler molecules arranged in the interstices between the predetermined straight lines together form an optically smooth area on the surface of the planar waveguide, the optically smooth area having the same refractive index and a uniform height relative to the outer surface of the planar waveguide that varies by no more than 1 nanometer.

2. The device according to claim 1, wherein the filler molecules are identical with the receptor molecules except that the filler molecules are deactivated so as to be incapable of binding the target molecules to the filler molecules.

3. The device according to claim 1, wherein the grating is arranged on the outer surface of the planar waveguide opposite to the substrate.

4. The device according to claim 1, wherein a minimum distance dmin between adjacently arranged straight parallel lines of the plurality of straight parallel lines, measured in the predetermined propagation direction, is defined according to the equation $$d\min = \lambda/(N - n_c \sin \alpha)$$

wherein
        $\alpha$ is a longitudinal angle between the predetermined detection direction and a normal to the outer surface of the planar waveguide, measured in the predetermined propagation direction,
        $\lambda$ is the vacuum wavelength of the coherent light,
        N is the effective refractive index of the coherent light propagating through the planar waveguide, and
        $n_c$ is the refractive index of a medium on the outer surface of the planar waveguide,
    and wherein the adjacently arranged straight parallel lines of the plurality of straight parallel lines are arranged at a distance d from each other which is an integer multiple of the minimum distance dmin.

5. The device according to claim 4, wherein the distance d between the adjacently arranged straight parallel lines of the plurality of straight parallel lines, measured in the predetermined propagation direction, is in the range of $\lambda/2 < d < 2\lambda/3$, or is an integer multiple thereof.

6. The device according to claim 4, wherein the longitudinal angle $\alpha$ is in the range of $1° < \alpha < 20°$.

7. The device according to claim 1, wherein an angle β between the straight parallel lines and the predetermined propagation direction of the coherent light, measured in the plane of the planar waveguide, is between 60° and 120°, preferably between 75° and 105°.

8. The device according to claim 1, further comprising a plurality of spatially separated decouplers arranged on the outer surface of the planar waveguide opposite to the substrate, each spatially separated decoupler having a said plurality of straight parallel lines, with the receptor molecules being arranged along the respective plurality of straight parallel lines and with the filler molecules being arranged in the interstices between the respective plurality of straight parallel lines.

9. The device according to claim 4, wherein the adjacent straight parallel lines of the plurality of straight parallel lines of at least one spatially separated decoupler of the plurality of spatially separated decouplers are arranged at a first distance $d_1$ from each other which is an integer multiple of a first minimum distance $d_{min1}$, wherein further the adjacent straight parallel lines of the plurality of straight parallel lines of at least one other spatially separated decoupler of the plurality of spatially separated decouplers are arranged at a second distance $d_2$ from each other which is an integer multiple of a second minimum distance $d_{min2}$, and wherein the first minimum distance $d_{min1}$ and the second minimum distance $d_{min2}$ are different from each other.

10. The device according to claim 7, wherein the straight parallel lines of at least one spatially separated decoupler of the plurality of spatially separated decouplers include a first angle $\beta_1$ with the predetermined propagation direction of the coherent light in the planar waveguide, and wherein the straight parallel lines of at least one other spatially separated decoupler of the plurality of spatially separated decouplers include a second angle $\beta_2$ with the predetermined propagation direction of the coherent light in the planar waveguide, wherein the first angle $\beta_1$ is different from the second angle $\beta_2$.

11. The device according to claim 8, wherein at least one spatially separated decoupler of the plurality of spatially separated decouplers has a first type of the receptor molecules capable of binding a first type of the target samples, and wherein at least one other spatially separated decoupler of the plurality of spatially separated decouplers has a second type of the receptor molecules capable of binding the first type of the target samples or a second type of the target samples, wherein the first type of the receptor molecules is different from the second type of the receptor molecules.

12. The device according to claim 8, further comprising a plurality of spatially separated sections on the outer surface of the planar waveguide opposite to the substrate, each spatially separated section comprising one or more of said spatially separated decouplers and a said grating.

13. The device according to claim 1, comprising a hydrogel layer arranged on the outer surface of the planar waveguide opposite to the substrate and covering the receptor molecules, the hydrogel layer being configured to allow the target samples to diffuse therethrough for allowing them to bind to the receptor molecules, the hydrogel layer further being configured to prevent molecules exceeding a predetermined size which is larger than the size of the target samples from diffusing therethrough.

14. The device according to claim 13, wherein in an area where the grating is arranged, a cover layer is arranged on the outer surface of the planar waveguide opposite to the substrate, the cover layer being transparent to the coherent light of the predetermined wavelength, and wherein an absorption layer is arranged on the transparent cover layer, the absorption layer being absorptive to the coherent light of the predetermined wavelength.

15. The device according to claim 1, wherein an outer surface of the planar waveguide opposite to the outer surface on which the receptor molecules are arranged is covered with an anti-reflection coating.

16. A system for the detection of binding affinities comprising
a device according to claim 1,
a light source for emitting coherent light of a predetermined wavelength, the light source and the device being arranged relative to one another such that the coherent light emitted from the light source is coupled into the planar waveguide via the grating of the device,
a lens for focusing the collimated beam of diffracted coherent light propagating away from the planar waveguide into a focal point,
a detector positioned optically downstream of the lens in the focal point of the lens, for detecting the diffracted coherent light of the collimated beam focused into the focal point of the lens, and
an evaluation device for providing a signal representative of the diffracted coherent light detected by the detector, the signal being indicative of the binding affinity of the target samples to the receptor molecules.

17. The system according to claim 16, further comprising a scanner and de-scanner being arranged in an optical path between the light source and the planar waveguide for directing the coherent light emitted from the light source towards the grating in a direction such that the amount of the coherent light coupled into the planar waveguide is maximal.

18. The system according to claim 16, further comprising a mirror having a front surface which is configured to reflect the collimated beam of diffracted coherent light towards the lens, and having a rear surface which is configured to allow the coherent light emitted from the light source to pass through the mirror, the mirror being arranged in an optical path of the diffracted coherent light between the scanner and de-scanner and the lens and in an optical path of the coherent light emitted from the light source between the light source and the scanner and de-scanner.

19. The system according to claim 17, wherein the scanner and de-scanner comprises a pivotable mirror and a telescopic lens arrangement having two further lenses arranged in an optical path of the diffracted coherent light between the planar waveguide and the pivotable mirror, the system further comprising an additional mirror arranged in an optical path of the coherent light emitted from the light source between the light source and the pivotable mirror, the additional mirror being configured to reflect the coherent light emitted from the light source and further being configured to allow the collimated beam of diffracted coherent light to pass through the additional mirror.

20. The system according to claim 16 the system further comprising an actuator for consecutively positioning the optical coupler of each spatially separated section of a plurality of spatially separated sections of the device in the path of the coherent light emitted from the light source such that the coherent light emitted from the light source is consecutively coupled into the planar waveguide at the respective spatially separated section.

21. The system according to claim 16 wherein the system comprises a diaphragm which is arranged such that light emitted from the light source must pass through the diaphragm, the diaphragm comprising a plurality of spatially separated transparent sections, each of the transparent sections of the plurality of spatially separated transparent sections of the diaphragm directing light emitted from the light source towards a different section of the plurality of spatially separated sections of the device.

22. The system according to claim 16, further comprising at least one magnet which is movably arranged for being positioned at a first position corresponding to the position of the decoupler but on a side of the planar waveguide opposite to the side where the receptor molecules are arranged on the surface of the planar waveguide, at a second position also corresponding to the position of the decoupler but on the same side of the planar waveguide where the receptor molecules are arranged on the surface of the planar waveguide, or at a third position in which the magnet is arranged remote from the path of the coherent light from the light source to the grating as well as remote from the path of the collimated beam of diffracted coherent light from the planar waveguide to the detector, and remote from the path of the coherent light from the grating to the decoupler.

* * * * *